United States Patent [19]

Ledley et al.

[11] Patent Number: 5,770,580

[45] Date of Patent: Jun. 23, 1998

[54] SOMATIC GENE THERAPY TO CELLS ASSOCIATED WITH FLUID SPACES

[75] Inventors: Fred D. Ledley; Bert W. O'Malley, Jr., both of Houston, Tex.

[73] Assignee: Baylor College of Medicine, Houston, Tex.

[21] Appl. No.: 453,501

[22] Filed: May 30, 1995

Related U.S. Application Data

[60] Division of Ser. No. 184,547, Jan. 21, 1994, which is a continuation-in-part of Ser. No. 181,707, Jan. 13, 1994, abandoned, which is a continuation-in-part of Ser. No. 912,934, Jul. 13, 1992, abandoned, and a continuation-in-part of Ser. No. 868,061, Apr. 13, 1992, abandoned.

[51] Int. Cl.$^6$ .................... A61K 31/735; C12P 21/02; C12N 15/64; C12N 5/16

[52] U.S. Cl. ................. 514/44; 435/69.1; 435/172.3; 435/320.1; 435/325

[58] Field of Search ................. 424/184.1; 425/69.3, 425/172.1; 514/44; 935/23, 55; 435/69.1, 172.3, 320.1, 325

[56] References Cited

U.S. PATENT DOCUMENTS

| | | | |
|---|---|---|---|
| 4,751,180 | 6/1988 | Cousens et al. | 435/69.7 |
| 5,166,320 | 11/1992 | Wu et al. | 530/395 |
| 5,175,146 | 12/1992 | Basava et al. | 514/12 |
| 5,194,654 | 3/1993 | Hostetler et al. | 558/152 |
| 5,223,263 | 6/1993 | Hostetler et al. | 424/450 |
| 5,580,859 | 12/1996 | Felgner et al. | 514/44 |
| 5,589,466 | 12/1996 | Felgner et al. | 514/44 |

FOREIGN PATENT DOCUMENTS

| | | |
|---|---|---|
| 90/11092 | 10/1990 | WIPO . |
| 90/14074 | 11/1990 | WIPO . |
| 91/16024 | 10/1991 | WIPO . |
| 91/17424 | 11/1991 | WIPO . |
| 9211359 | 7/1992 | WIPO . |
| 93/03709 | 3/1993 | WIPO . |
| 93/14778 | 8/1993 | WIPO . |

OTHER PUBLICATIONS

Marshall Gene therapy's growing pains Science vol. 269 1050–1055, 1995.
Orkin et al. Report and recommendations of the panel to assess the NIH investment in research on gene therapy, pp. 1–40, 1995.
Anderson, "Prospects for Human Gene Therapy," 226 *Science* 401, 1984.
Anderson, "Human Gene Therapy," 256 *Science* 808, 1992.
Ascadi et al., "Human Dystrophin Expression in mdx Mice After Intramuscular Injection of DNA Constructs," 352 *Nature* 815, 1991.
Asher et al., "Murine Tumor Cells Transduced with the Gene for Tumor Necrosis Factor–α," 146 *J. Immunol.* 3227, 1991.
Bandara et al., "Gene Transfer to Synoviocytes: Prospects for Gene Treatment of Arthritis," 11(3) *DNA and Cell Biology* 227, 1992.

Bell et al., "Reconstruction of a Thyroid Gland Equivalent From Cells and Matrix Materials," 232 *J. Exp. Zoology* 277, 1984.
Bonnerot "A β–Galactosidase Hybrid Protein Targeted to Nuclei as a Marker for Developmental Studies," 84 *PNAS* 6795, 1987.
Cornetta et al., "Safety Issues Related to Retroviral–Mediated Gene Transfer in Humans," 2 *Hum. Gen. Ther.* 5, 1991.
Culver et al., "Lymphocyte Gene Therapy," 2 *Hum. Gen. Ther.* 107, 1991.
Curiel et al., "Adenovirus Enhancement of Transferrin–polylysine–mediated Gene Delivery," 88 *PNAS* 8850, 1991.
Dingle et al., "A Cartilage Catabolic Factor From Synovium," 184 *Biochem. J.* 177, 1979.
Felgner et al., "Lipofection: A Highly Efficient, Lipid–Mediated DNA–Transfection Procedure," 84 *PNAS* 7413, 1987.
Firestein et al., "Quantitative Analysis of Cytokine Gene Expression in Rheumatoid Arthritis," 144 *J. Immunol.* 3347, 1990.
Friedmann, "Progress Toward Human Gene Therapy," 244 *Science* 1275, 1989.
Hubbard et al., "Effect of Purified Human Interleukin–1 on Cartilage Degradation," 6 *J. Orthop. Res.* 180, 1988.
Jaffe et al., "Adenovirus–Mediated In Vivo Gene Transfer and Expression in Normal Rat Liver," 1 *Nature Genetics* 372, 1992.
Jiao et al., "Direct Gene Transfer into Nonhuman Primate Myofibers In Vivo," 3 *Hum. Gen. Ther.* 21, 1992.
Ledley, "Somatic Gene Therapy in Gastroenterology: Approaches and Applications," 14 *J. Pediatr. Gast. Nutr.* 328, 1992.
Ledley, "Hepatic Gene Therapy: Present and Future," 18 *Hepatology* 1263, 1993.
Ledley, "Are Contemporary Methods for Somatic Gene Therapy Suitable for Clinical Applications?" 16 *Clin. Invest. Med.* 78, 1993.
Ledley, "Human Gene Therapy," Jacobson and Jolly vol. Eds., *Biotechnology*, vol 7b Gene Technology, Munich: VCH Verlagsgesellschaft, 401–457, 1989.
Lem et al., "Retinal Degeneration is Rescued in Transgenic rd Mice by Expression of the cGMP Phosphodiesterase β Subunit," 89 Proc. Natl. Acad. Sci. USA 4422, 1992.

(List continued on next page.)

*Primary Examiner*—James Ketter
*Assistant Examiner*—John S. Brusca
*Attorney, Agent, or Firm*—Lyon & Lyon LLP

[57] ABSTRACT

This invention relates to somatic gene therapy to cells associated with fluid spaces, such as follicles of the thyroid, the synovium of the joint, the vitreous of the eye and the inner or middle ear. Formulated DNA expression vectors are introduced with or without formulation elements into fluid spaces under conditions in which cells associated with the fluid space can incorporate the formulated DNA expression vector. Formulated DNA expression-mediated gene therapy allows treatment of diseases involving cells associated with fluid spaces.

14 Claims, 8 Drawing Sheets

OTHER PUBLICATIONS

Levick, "Permeability of Rheumatoid and Normal Human Synovium to Specific Plasma Proteins," 24 *Arthritis Rheum.* 1550, 1981.

Lafferty et al., "Mechanism of Thyroid Allograft Rejection," 54 Aust. J. Exp. Biol. Med. Sci. 573,1976.

Lin et al., "Expression of Recombinant Genes in Myocardium In Vivo After Direct Injection of DNA," 82 *Circulation* 2217, 1990.

MacGregor, "Histochemical Staining of Clonal Mammalian Cell Lines Expressing *E. Coli* β Galactosidase Indicates Heterogenous Expression of the Bacterial Gene," 13 *Somat. Cell. Mol. Genet.* 253, 1987.

McDonnell, et al., "Nuclear Hormone Receptors as Targets for New Drug discovery," *BioTechniques* 11:1256–1261 (1993).

Miller and Rosman, "Improved Retroviral Vectors for Gene Transfer and Expression," 7(9) *BioTechniques* 980, 1989.

Miller, "Human Gene Therapy Comes of Age," 357 *Nature* 455, 1992.

Miossec et al., "Interleukin–1 Lymphocyte Chemotactic Activity in Rheumatoid Arthritis Synovial Fluid," 29 *Arthritis Rheum.* 461, 1986.

Moolten and Cupples, "A Model for Predicting the Risk of Cancer Consequent to Retroviral Gene Therapy," 3 *Hum. Gen. Ther.* 479, 1992.

Morgan et al., "Applications of the Polymerase Chain Reaction in Retroviral–Mediated Gene Transfer and the Analysis of Gene–Marked Human TIL Cells," 1 *Hum. Gen. Ther.* 135, 1990.

Morgan et al., "Expression of an Exogenous Growth Hormone Gene by Transplantable Human Epidermal Cells," 237 *Science* 1476, 1987.

Mulligan, "The Basic Science of Gene Therapy," 260 *Science* 926, 1993.

Nabel et al., "Recombinant Gene Expression In Vivo Within Endothelial Cells of the Arterial Wall," 244 *Science* 1342, 1989.

Nicolau and Cudd, "Liposomes as Carriers of DNA," 6 *Crit. Rev. Ther. Drug Carrier Syst.* 239, 1989.

O'Malley, Jr. and Ledley, "Somatic Gene Therapy in Otolaryngology–Head and Neck Surgery," 119 *Arch. Otolaryngol. Head Neck Surg.* 1191, 1993.

Olsson et al., "Transgenic Mice with a Rhodopsin Mutation (Pro23His): A Mouse Model of Autosomal Dominant Retinitis Pigmentosa," 9 *Neuron* 815, 1992.

Palmer et al., "Genetically Modified Skin Fibroblasts Persist Long After Transplantation but Gradually Inactivated Introduced Genes," 88 *Proc. Natl. Acad. Sci. USA* 1330, 1991.

Peter et al., "Comparison of FRTL–5 Cell Growth In Vitro with That of Xenotransplanted Cells and the Thyroid of the Recipient Mouse," 128 *Endocrin.* 211, 1991.

Pettipher et al., "Interleukin 1 Induces Leukocyte Infiltration and Cartilage Proteoglycan Degradation in the Synovial Joint," 83 Proc. Natl. Acad. Sci. USA 8749, 1986.

Quantin et al., "Adenovirus as an Expression Vector in Muscle Cells In Vivo," 89 *Proc. Natl. Acad. Sci. USA* 2581, 1992.

Rosenberg et al., "Gene Transfer Into Humans—Immunotherapy of Patients with Advanced Melanoma, Using Tumor–Infiltrating Lymphocytes Modified by Retroviral Gene Transduction," 323 *New Engl. J. Med.* 570, 1990.

Rosenberg, "Gene Therapy for Cancer," 268 J. Am. Med. Assoc. 2416, 1992.

Rosenfeld et al., "A Null Mutation in the Rhodopsin Gene Causes Rod Photoreceptor Dysfunction and Autosomal Recessive Retinitis Pigmentosa," 1 *Nature Genet.* 209, 1992.

Rosenfeld et al., "In Vivo Transfer of the Human Cystic Fibrosis Transmembrane Conductance Regulator Gene to the Airway Epithelium," 68 *Cell* 143, 1992.

Scharfmann et al., "Long–term In Vivo Expression of Retrovirus–mediated Gene Transfer in Mouse Fibroblast Implants," 88 *Proc. Natl. Acad. Sci. USA* 4626, 1991.

Sikes, et al., "In Vivo and Ex Situ Gene Transfer to the Thyroid for Somatic Gene Therapy in Animal Models," *Am. J. Hum. Gen.* 51:A227, Abstract 894 (1992).

Sikes, et al., "In Vivo Gene Transfer into Rabbit Thyroid b Direct DNA Injection: A Novel Strategy for Gene Therapy," *J. Cell. Biochem.* 17E:208, Abstract S 315 (1993).

Skolnik et al., "Autotransplantation in Lingual Ectopia of Thyroid Gland," 78 *Arch. Otolaryngol.* 187, 1963.

Swan et al., "Thyroid Autograft," 94 *Arch. Surg.* 817, 1967.

Legendre and Szoka, Jr., "Cyclic Amphipathic Peptide–DNA Complexes Mediate High–Efficiency Transfection of Adherent Mammalian Cells," 90 Proc. Natl. Acad. Sci. USA 893, 1993.

Chu et al., "Efficiency of Cytoplasmic Delivery of pH–Sensitive Liposomes to Cells in Culture," 7 *Pharm. Res.* 824, 1990.

Haensler and Szoka, Jr., "Synthesis and Characterization of a Trigalactosylated Bisacridine Compound to Target DNA To Hepatocytes," 4 *Bioconjug. Chem.* 85, 1993.

Legendre and Szoka, Jr., "Delivery of Plasmid DNA into Mammalian Cell Lines Using pH–Sensitive Liposomes: Comparison with Cationic Liposomes," 9 *Pharm. Res.* 1235, 1992.

Talmage et al., "Activation of Transplant Immunity: Effect of Donor Leukocytes on Thyroid Allograft Rejection," 191 *Science* 385, 1976.

Travis et al., "Complete Rescue of Photoreceptor Dysplasia and Degeneration in Transgenic retinal degeneration slow (rds) Mice," 9 *Neuron* 113, 1992.

Wagner et al., "Transferrin–Polycation Conjugates as Carriers for DNA Uptake into Cells," 87 *PNAS* 3410, 1990.

Wallis and Simkin, "Antirheumatic Drug Concentrations in Human Synovial Fluid and Synovial Tissue: Observations on Extravascular Pharmacokinetics," 8 *Clin. Pharmacokinet.* 496, 1983.

Wallis et al., "Protein Traffic in Human Synovial Effusions," 30 *Arthritis Rheum.* 57, 1987.

Wertz, "Management of Undescended Lingual and Subhyoid Thyroid Glands," 84 *Laryngoscope* 507, 1974.

Westacott et al., "Synovial Fluid Concentration of Five Different Cytokines in Rheumatic Diseases," 49 *Ann. Rheum. Dis.* 676, 1990.

Wilson et al., "Temporary Amelioration of Hyperlipidemia in Low Density Lipoprotein Receptor–Deficient Rabbits Transplanted with Genetically Modified Hepatocytes," 87 Proc. Natl. Acad. Sci. USA 8437, 1990.

Wagner et al., "Transferrin–Polycation–DNA Complexes. The Effect of Polycations on the Structure of the Complex and DNA Delivery to Cells," 88 Proc. Natl. Acad. Sci. USA 4255, 1991.

Wolff et al., "Conditions Affecting Direct Gene Transfer into Rodent Muscle In Vivo," 11(4) *Biotechniques* 474, 1991.

Wolff et al., "Direct Gene Transfer into Mouse Muscle In Vivo," 247 *Science* 1465, 1990.

Wolff et al., "Expression of Naked Plasmids by Cultured Myotubes and Entry of Plasmids into T Tubules and Caveolae oe Mammalian Skeletal Muscle," 103 *J. Cell Science* 1249, 1992.

Wood et al., "Release of Interleukin–1 From Human Synovial Tissue In Vitro," 28 *Arthritis Rheum.* 853, 1985.

Wu and Wu, "Evidence for Targeted Gene Delivery to Hep G2 Hepatoma Cells In Vitro," 27 *Biochem.* 887, 1988.

Yang et al., "In Vivo and In Vitro Gene Transfer to Mammalian Somatic Cells by Particle Bombardment," 87 Proc. Natl. Acad. Sci. USA 9568, 1990.

Zack, "Ocular Gene Therapy: From Fantasy to Foreseeable Reality," *Archives of Ophthalmology* 111:1477–1479 (1993).

Zack et al., "Unusual Topography of Bovine Rhodopsin Prometer–lacZ Fusion Gene Expression in Transgenic Mouse Retinas," 6 *Neuron* 187, 1991.

FIG. 3.
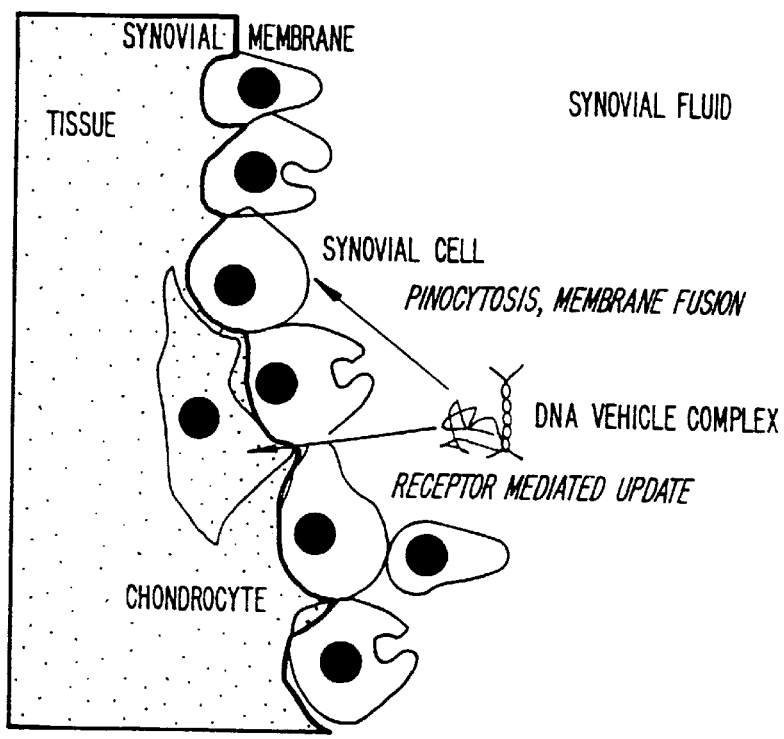
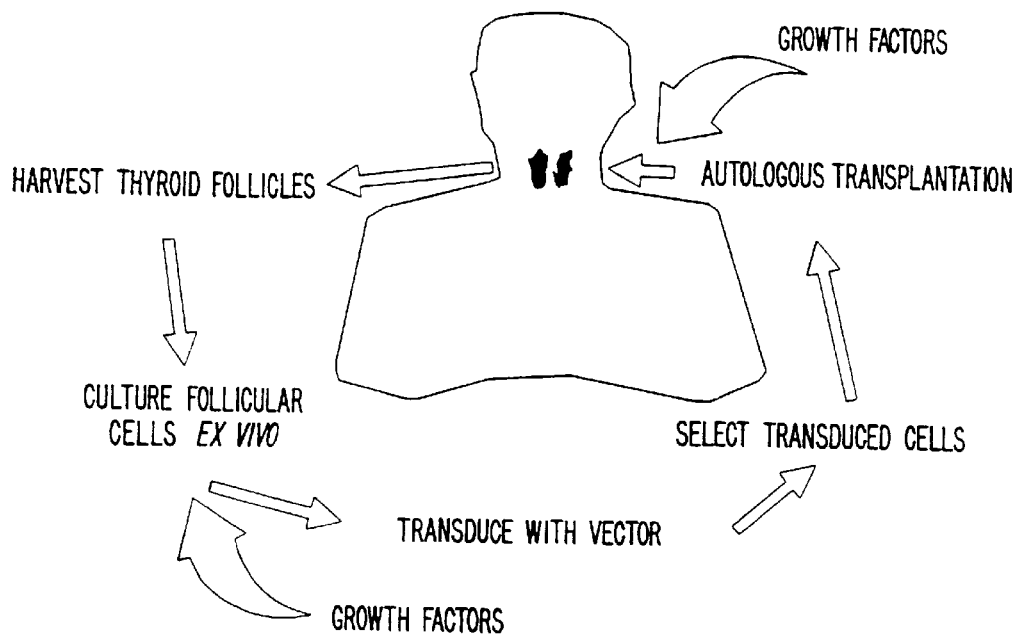
FIG. 4.

Direct Injection of viral vectors with pharmacological or endocrine stimulation of thyroid growth.

Direct injection of plasmid expression vector in solution or with carrier

Injection of plasmid vector complexed to thyrotropic proteins.

FIG. 7.

- ■ LONG TERMINAL REPEAT SEQUENCES (LTR)
- ☐ ψ PACKAGING SEQUENCES
- ▨ SELECTABLE MARKER (OPTIONAL)
- ⌈┈⌉ PROMOTOR FOR REGULATED THYROID TRANSCRIPTION
- ▨ NUCLEIC ACID CASSETTE (cDNA, OTHER SEQUENCE)
- ▨ OTHER RETROVIRAL SEQUENCES (VARIABLE POSITION)

FIG. 8.

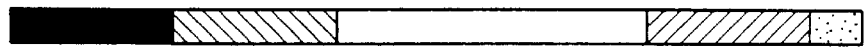

TRANSCRIPTION →

TRANSLATION →

- ■ PROMOTOR FOR PROPER TRANSCRIPTION IN THYROID
- ▨ GENOMIC SEQUENCES INCLUDING INTRON
- ☐ NUCLEIC ACID CASSETTE (OPEN READING FRAME)
- ▨ 3' UNTRANSLATED REGION
- ▨ POLYADENYLATION SEQUENCES

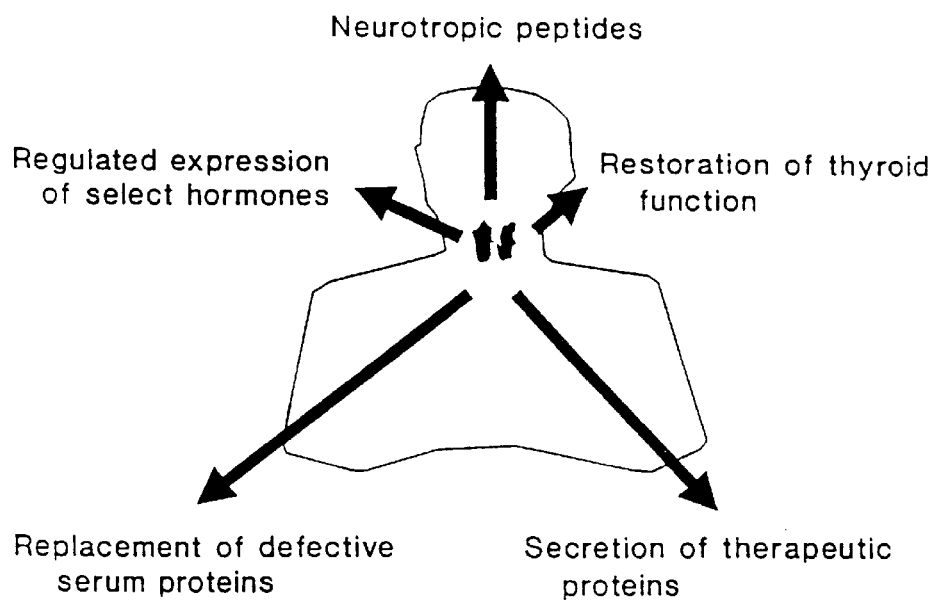

FIG. 9.

SOMATIC GENE THERAPY TO CELLS ASSOCIATED WITH FLUID SPACES

This application is a divisional of application Ser. No. 08/184,547, by Ledley et al., filed Jan. 21, 1994, entitled "Somatic Gene Therapy to Cells Associated with Fluid Spaces." The 08/184,547 application is a continuation-in-part of Ledley et al., application Ser. No. 08/181,707, now abandoned, filed Jan. 13, 1994, entitled "Somatic Gene Therapy." Both the above referenced continuation-in-part applications are hereby incorporated by reference (including drawings). In addition, the 08/181,707 application is also a continuation-in-part of Ledley, application Ser. No. 07/912,934, now abandoned filed Jul. 13, 1992, entitled "Targeting Somatic Gene Therapy to the Joints," and also a continuation-in-part of Ledley et al., application Ser. No. 07/868,061, now abandoned, filed Apr. 13, 1992, entitled "Targeting Somatic Gene Therapy to the Thyroid," the whole of which (including drawings) are both hereby incorporated by reference.

BACKGROUND OF THE INVENTION

This invention relates to somatic gene therapy to cells associated with fluid spaces within the joints, thyroid, ear and eye.

Somatic gene therapy involves the treatment of inherited or acquired disease by the introduction of recombinant genes into somatic cells (i.e., those cells that constitute the organs of the body) to express therapeutic gene products. (Anderson, W. F., Science, 226:401–409 (1984); Friedmann, T., Science, 244:1275–1278 (1989); Ledley, F. D., Jacobson G. Ed. Biotechnology, Munich:Vch Verlagsgesellschaft, 401–457 (1989)). Different organs have been considered targets for somatic gene therapy including the bone marrow, lymphocytes, liver, muscle, skin and fibroblasts. (Rosenberg, S. A. et al., New Engl. J. Med., 323:570–578 (1990); Ledley, F. D., J. Pediatr. Gast. Nutr. (1992); Nabel, E. G. et al., Science 244:1342–1344 (1989); Morgan, J. R. et al., Science, 237:1476–1479 (1987); Palmer, T. D. et al., PNAS, 88:1330–1334 (1991); Scharfmann, R. et al., PNAS, 88:4626–4630 (1991); Ascadi, G. et al., Nature, 352:815–818 (1991)). Studies regarding somatic gene therapy have involved in vitro or ex vivo techniques. These ex vivo studies focused on the harvesting of cells from a tissue by a surgical biopsy, isolating and growing the cells in culture, introducing genes into the cells using viral vectors, and then reimplanting these cells into the body by autologous transplantation procedures. (Rosenberg, S. A., JAMA, 268:2416–2419 (1992); Miller, A. D., Nature, 357:455–460 (1992); Anderson, W. F., Science, 256:808–813 (1992)). A number of viral-mediated gene transfer systems have been experimented with including retroviruses, herpes viruses, adenoviruses, adeno-associated viruses and papilloma viruses. (Culotta, E., et al., Science, 260:914–915 (1993); Anderson, W. F., et al., Science, 256:808–813 (1992); Miller, A. D., et al., Nature, 357:455–460 (1992); Mulligan, R. C., et al., Science, 260:926–932 (1993)).

Recombinant genes have been introduced into circulating tumor infiltrating lymphocytes to study the localization of tumor infiltrating lymphocytes and to deliver tumor necrosis factor to solid tumors. (Rosenberg, S. A., New Engl. J. Med., 323:570–578 (1990); Asher, A. L. et al., J. Immunol., 146:3227–3234 (1991)). Other gene therapy deliveries have utilized viral-mediated delivery of genes to peripheral blood lymphocytes and bone marrow to treat severe combined immune deficiency due to adenosine deaminase deficiency. (Culver, K. W. et al., Hum. Gen. Ther., 2:107–109 (1991)). Other studies have also utilized viral-mediated gene transfer to deliver lowdensity lipoprotein receptor to hepatocytes. (Wilson, J. M. et al., P.N.A.S., 87:8437–8441 (1990)).

With respect to gene therapy to the joints, retro-viruses have been utilized for gene delivery to synoviocytes of the joints. (Bandara, G., et al., Chem. Abstracts, Vol. 117.97 W (1992); Bandara, G. et al., DNA and Cell Biology, 11:3:227–231 (1992)). These studies utilize retroviral vectors capable of expressing lacZ and neo genes in synovial fibroblasts in vitro. Neo-selected cells carrying the lacZ marker gene were transplanted back into the knees of recipient rabbits. Id. These studies then examined the expression of these genes in vivo.

Use of viral-mediated gene transfer to the joints has focused on the treatment of arthritis with interleukin-1 (IL-1) receptor. The IL-1 protein is an important mediator of joint pathology. It is produced by the arthritic synovium. (Wood, D. D. et al., Arthritis Rheum., 28:853–862 (1985); Firestein, G. S., et al., J. Immunol., 144: 3347–3353 (1990)). Studies have measured IL-1 in synovial fluid. (Miossec, P., et al., Arthritis Rheum., 29:461–470 (1986); Westacott, C. I., et al., Ann. Rheum. Dis., 49:676–681 (1990)). IL-1 produces synovial inflammation, cartilage breakdown and bone resorption. (Dingle, J. T., et al., Biochem. J., 184:177–180 (1979); Hubbard, J. R. et al., J. Orthop. Res., 6:180–187 (1988); Pettipher, E. R. et al., PNAS, 83:8749–8753 (1986)).

PCT Publication US91/09231 entitled, "A Truncated Interleukin-1 Receptor Gene for the Treatment of Arthritis", (Glorioso, C. et al.) discloses treatment of arthritic conditions due to IL-1 using retroviral vectors carrying the therapeutic IL-1 receptor gene and a selectable marker. These researchers noted that synovial cells from a patient's joint can be removed and transduced with the above vector. Id. Therapeutic autologous cells could then be reintroduced back into the joint of the patient by cellular transplantation techniques. Id.

With respect to gene transfer to the thyroid, Cone, R. D. et al., (Mol. Cell. Bio., 8:1036–1044 (1988)) utilized adenoviral transforming genes incorporated in retroviral vectors to study epithelial cell transformation. These studies disclose that adenoviral genes can be used to induce proliferation and immortalization of epithelial cells. Id. The authors disclose that rat kidney, liver, heart, pancreas and thyroid cultures can be transduced with the viral vector, however, they were not successful in introducing genes into each of these cell types. Retrovirus vectors carrying the adenovirus EIA oncogene and the neomycin phosphotransferase gene have been used to establish transformed fetal human thyroid-derived cell lines. (Cone, R. D., et al., Endocrin., 123 :2067–2074 (1988)). These cell lines were used to study in vitro regulation of major histocompatibility class II genes of the thyroid. Id.

In addition to the above, separate studies have been performed involving thyroid tissue transplantation. Investigators have studied autologous transplantation of intact thyroid tissue as a means for preventing hypothyroidism after surgical removal of lingual thyroid or other ectopic gland tissue. (Wert, M. L., Laryngoscope, 84:507–521 (1974); Skolnik, E. M., Arch. Otolaryngol., 78:187–91 (1963); Swan, H. et al., Arch. Surg., 94:817–20 (1967)). Researchers have also reported allogenic transplantation of thyroid tissue or tissue maintained in organ culture. (Lafferty, K. J. et al., Aust. J. Exp. Biol. Med. Sci., 54:573–86 (1976); Talmage, D. W. et al., Science, 191:385–89 (1976)). Reports have also described transplantation of cells from immortalized thyroid-like cell lines and reconstruction of the follicular unit. (Peter, H. J., Endocrin., 128:211–19 (1991); Bell, E., J. Exp. Zoology, 232:277–85 (1984)).

With respect to the eye, studies involving ocular gene therapy have involved germ line transformations. Murine retinal degeneration and retinal degeneration "slow" mutations have been avoided using transgenic mouse technology. (Lem, J., et al., PNAS, 15:4422–4426 (1992); Travis, G. H. et al., Neuron, 9:113–119 (1992)). Particular ocular diseases have also been correlated to defective genes. Studies utilizing transgenic mice have studied these underlying genetic defects causing ocular diseases. (Zack, D. J., et al., Neuron, 6:187–199 (1991)). For example a null mutation in the rhodopsin gene causes rod photoreceptor disfunction and autosomal recessive retinitis pigmentosa. (Rosenfeld, P. et al., Nature Genet., 1:209–213 (1992)). By using transgenic mice with rhodopsin mutations, mouse models can be used to study autosomal dominant retinitis pigmentosa. (Olsson, J. E. et al., Neuron, 9:815–830 (1992)). In addition, retroviral vectors have been injected into the retina of fetal animals to study cellular differentiation (Cepko, et al., supra).

In addition to retroviruses, recombinant adenoviruses have been demonstrated to mediate expression of foreign transgenes in vivo in a variety of terminally differentiated cell types including neurons, glia, pulmonary epithelium, hepatocytes and skeletal muscle. (Rosenfeld, M. A., et al., Cell, 68:143–155 (1992); Jaffe, H. A., et al., Nature Genetics, 1:372–378 (1992); Quantin, B., et al., P.N.A.S. 89:2581–2584 (1992)).

Studies involving direct injection of "naked" DNA have focused on muscle and heart tissue. These studies disclosed that direct injection of DNA into skeletal or cardiac muscle expresses high levels of reporter genes (Wolff, J. A. et al., Science, 247:1465–1468 (1990); Wolff, J. A. et al., Biotechniques, 11:474–85 (1991); Jiao, S. et al., Hum. Gen. Ther., 3:21–23 (1992); Lin, H. et al., Circulation, 82:2217–2221 (1990)). These studies and others revealed that this is an unusual property of muscle and that DNA injections into other solid tissues does not result in gene expression at the same order of magnitude as muscle. Other strategies for DNA delivery involve use of ligand/DNA complexes, cationic lipids, liposomes or DNA-coated microparticle bombardment. (Wu, G. V. et al., Biochem., 27:887–92 (1988); Wagner, E. et al., P.N.A.S. 87:3410–3414 (1990); Wagner, E. et al., P.N.A.S. 88:4255–4259 (1991); Curiel D. T. et al., P.N.A.S., 88:8850–8854 (1991); Felgner, P. L. et al., P.N.A.S. 84:7413 (1987); Nicolau, C. et al., Crit. Rev. Ther. Drug Carrier Syst., 6:239–271 (1989); Yang, N. S. et al., P.N.A.S. 87:9568–72 (1990)).

SUMMARY OF THE INVENTION

Applicant has surprisingly determined that it is useful to construct formulated DNA expression vectors which can be introduced directly into fluid spaces such that cells associated with the fluid space can incorporate the vector construct and express the recombinant gene. No other studies have tried or considered direct injection of formulated DNA expression vectors to cells associated with fluid spaces such as the follicles of the thyroid, the synovium of the joint, the vitreous of the eye and the inner or middle ear. The present invention discloses expression of recombinant genes in the above tissues at levels similar or the same as expression seen in muscle. This method of gene delivery is unique to the tissues associated with fluid spaces and in light of the prior art delivery by this method was completely unexpected.

The above method of gene therapy is useful in delivering therapeutic genes to cells associated with fluid spaces such as the follicles of the thyroid, the synovium of the joint, the vitreous of the eye, the inner or middle ear. These formulated DNA expression vectors can be used to treat diseases affecting these organs by delivering the vectors that express therapeutic gene products. These formulated DNA expression vectors can be used to treat diseases affecting other organs by delivering vectors that express a therapeutic gene product that is secreted into the systemic circulation. These vectors can also be used to create animal models for assessing the pathogenesis of human disease and accordingly understanding how to perform gene therapy. Furthermore, this method of delivery can be used for producing immune responses associated with fluid spaces and discovering methods for treating immune mediated disease.

Prior to gene therapy, therapeutic treatment of diseases involving the joints has been hindered by the inability to specifically target drugs to the joint. Methods used required systemic administration causing high concentrations of drugs to be administered in order to reach intraarticular therapeutic doses. This also resulted in high concentrations of drugs in tissues other than the joint. Depending on the drug, high doses caused side effects. These methods of drug delivery to the joints depended upon vascular perfusion of the synovium to carry the drug to the joint. Perfusion was inefficient due to passive diffusion problems which restricted passage of large molecules, such as proteins, to the joints. (Bandara, et al., DNA and Cell Bio., 11: 227–231 (1992); Wallis, W. J., et al., Clin. Pharmacokinet., 8:496–522 (1983); Levick, J. R., Arthritis Rheum., 24:1550–1560 (1981); Wallis, W. J., et al., Arthritis Rheum., 30:57–63 (1987)). Researchers have tried intraarticular injection to avoid the above problems; however, materials introduced intraarticularly have a short half-life. (Bandara, P. D., et al., DNA and Cell Biol., 11:227–231 (1992)).

The use of formulated DNA expression vectors has a significant advantage in that very few molecules of the vector will be required for a therapeutic effect (i.e., each molecule expresses many copies of the therapeutic gene product). Furthermore, the formulated DNA expression vectors may provide controlled persistence of the therapeutic effect. The use of formulated DNA expression vectors for systemic administration has a significant advantage in that a tissue-specific promoter can be incorporated such that the therapeutic gene product is produced only in the joint or other target tissue even if the vector is distributed elsewhere, thus restricting the biological effect of the vector to the desired target.

As discussed above, others have attempted to introduce genes coding for proteins with antiarthritic properties into the synovium of the joint. Use of retroviruses to transfer genes via transplantation techniques directly into the synovial lining through intraarticular injection is limited by several factors. Although retroviral vectors are theoretically attractive vehicles for gene therapy, difficulties have been encountered in developing schemes using retroviral vectors for somatic gene therapy. First, in practice it is difficult to produce the large numbers of viral particles required for human experiments. (Ledley, F. D., Clin. Invest. Med., 16:78–88 (1993)). The production of high quality, high titer retroviral vectors free of potentially dangerous recombinants remains a challenging research and manufacturing problem. Id.

Second, directly injected retroviral vectors into the synovial lining are unable to infect synoviocytes in situ. (Bandara, G., et al., DNA and Cell Biol. 11:227–231

(1992)). The synovial lining is mitotically quiescent. Retroviruses require cell division for transduction. Id. Manipulation of the synoviocytes is required to permit retroviral infection. Id. Furthermore, retroviral transduction by this method does not permit the selection of which cells to be transduced. Id. Thus, the use of retroviral vectors does not permit direct delivery of the therapeutic vector to the patient, but rather requires use of ex vivo strategies for gene delivery.

Third, while methods for transplantation of bone marrow and epidermal cells are established in clinical practice, there is no clinical experience with the transplantation of other cell types including hepatocytes, fibroblasts, myoblasts, thyroid follicular cells, or synovial cells. Id. Cellular transplantation raises difficult questions concerning surgical delivery, engraftment, vascularization, differentiation, handling of large numbers of cells, and difficulty and expense of a large-scale primary cell culture. Id.

Fourth, profound difficulty has been encountered in achieving stable expression of recombinant genes in vivo after reimplantation. Experiments in bone marrow, fibroblasts, myoblasts, and hepatocytes have documented the loss of gene expression from the retroviral vector transduced cells within weeks after transplantation. (Palmer, T. D., et al., PNAS, 88:1330–1334 (1991)).

Viral-mediated gene transfer into synoviocytes using ex vivo methods is also limited in terms of its applicability to human therapy. Retroviral vector transduction of cells in vitro and reintroducing the transduced cells into the joints involves considerable technical complexities of synoviocyte transplantation, a procedure which has not been performed in human subjects.

Furthermore, there are a number of risks in the use of retroviral vectors for gene therapy. First, the possibility exists of activating proto-oncogenes near the site of integration or the possibility that the defective virus can recombine with wild-type virus to produce a novel infectious agent. (Ledley, F. D., Hepatology, 18:1263–1273 (1993); Cornetta, K., et al., Hum. Gen. Ther., 2:5–14 (1991); Moolten, F. L., et al., Hum. Gen. Ther., 5:479–486 (1992)). Second, since retroviral vectors persist indefinitely in the infected cell, there is no way to adjust to the patient's evolving clinical needs or terminate therapy if indicated by the patient's condition. Third, difficulty exists in achieving stable, regulated expression from retroviral vectors in cells that permanently carry the transduced gene. (O'Malley, B. W., Jr. et al., Arch. Otolarynogol. Head Neck Surg., 119:1191–1207 (1993)). Cells apparently are able to shut off expression from retroviral vectors under certain conditions. Id.

Another method which has been studied is the use of recombinant, attenuated adenoviral vectors to transform cells by in vivo infection. Id. Just as with retroviruses, there are risks in using adenoviruses. Adenoviral vector constructs are not completely defective and will express a series of viral gene products. Id. Under particular conditions, adenoviral vectors remain capable of inducing cell lysis and inflammatory responses. Id. This means such vectors are specifically unsuitable for gene therapy of disorders such as arthritis where cytopathicity may be a precursor to arthritis.

Other viral vectors used for viral-mediated gene therapy also have similar disadvantages. For example, herpes virus vectors are capable of infecting cells and persisting indefinitely in a latent state. Id. These viruses, however, are not completely defective and continue to express many viral proteins that can be cytopathic. Id. Adeno-associated viruses stably integrate in the genome and may have certain advantages over retroviral vectors in terms of their site of integration, but methods have not been described for producing these vectors in large quantities.

The use of nonviral DNA vectors has been limited to certain tissues in muscle (i.e., skeletal, cardiac, smooth) which take up DNA via its unique tubules system (Wolff, J. A. et al., J. Cell Science, 103:1249–1259 (1992)) and tissues where uptake is enhanced by certain protein carriers (Wu, G. V. et al., supra). To date, injection of nonviral DNA vectors into other organs does not produce expression of recombinant genes at levels similar to those seen in muscle. The present invention, however, has been able to achieve significant levels of expression by directly injecting formulated DNA vectors into cells associated with fluid spaces (e.g., joints, thyroid, ear, and eye) and express recombinant genes at levels comparable to levels seen in muscle.

Significantly, the kinetics of uptake and expression of the DNA vectors is distinctly different than the kinetics observed after administration of DNA directly to muscle or targeted delivery of DNA to other tissues. Such differences in kinetics suggest that the mechanism of uptake and expression is different in the present invention from methods described previously for other targets.

Taking advantage of the ability to directly inject formulated DNA expression vectors into fluid spaces, the present invention features gene therapy to cells associated with fluid spaces such as the follicles of the thyroid, the synovium of the joint, the vitreous of the eye and the inner or middle ear. Such therapy transfers DNA to organs not targeted by previous methods. This method for gene delivery is different than that required or useful for other organs. Unlike methods which use viral vectors, particularly retroviral vectors, the present invention allows use of genes as medicines that can be administered intermittently in response to acute disease or over the long term to establish steady state levels of a therapeutic gene product. Thus, genes can be used as medicines in the same way that organic compounds or proteins are currently used in clinical practice. This type of direct in vivo development can be applied to routine problems of medicine and surgery.

The advantages of the present invention allow treatment of particular diseases by nonviral-mediated gene therapy which involves delivery of formulated DNA vectors to cells associated with fluid spaces of the follicles of the thyroid, the synovium of the joint, the vitreous of the eye, and the inner or middle ear. In addition, the above method of gene therapy can be used to transform cells associated with the fluid spaces to produce particular proteins and RNA as well as used in methods for creating immune responses. In addition, the above method of gene therapy allows development of therapy for diseases that could not previously be treated by available methods for gene delivery. Furthermore, this method is clinically applicable as well as a nontoxic method of treating diseases. The present invention is also useful in creating animal models of disease in order to assess and explore novel therapeutic avenues.

It should also be noted that this invention features vectors in which nucleic acid sequences are expressed which code for genetically modified steroid receptors such as the glucocortico-mimetic receptor, a recombinant receptor related to those of the steroid receptor superfamily. The modified receptor, (e.g. glucocortico-mimetic) can be used to achieve steroid-like effects for the treatment of arthritis without the use of active steroids. In addition, this invention also features methods for ablation of inflammatory cells in a joint by introducing formulated DNA expression vectors into fluid spaces which are targeted for selective uptake by phagocytic cells within the joint.

The first aspect of the present invention features a method for gene therapy in which a formulated DNA expression vector is introduced into a fluid space. Under appropriate conditions, cells associated with the fluid space incorporate the vector into the cell. The vector includes a nucleic acid cassette, a 5' flanking region including necessary sequences for expression of the nucleic acid cassette, a linker connecting the 5' flanking region to the nucleic acid cassette in which the linker contains a position for inserting the nucleic acid cassette, and a 3' flanking region which is 3' to the position for inserting the nucleic acid cassette. In addition, the linker lacks the coding sequence of a gene with which it is naturally associated. That is, the linker is not the normal gene associated with the 5' and 3' regions.

The term "fluid space" as used herein refers to extracellular space enclosed by a cellular membrane. The fluid space is capable of containing fluid but need not actually contain fluid. It may therefore be what is known in the art of histology as a "potential space". Fluid or other material injected into the fluid space can be absorbed or resorbed by surrounding cells. The fluid or other material injected into the fluid space can also be removed from the space by surrounding cells through endocytosis or pinocytosis. The terms "endocytosis" and "pinocytosis" are used as they are known in the art. It includes, among other things, any mechanism by which cells take extracellular fluid into the cytoplasm. The fluid space for example can be the follicles of the thyroid or formed by the synovium of the joint, vitreous of the eye, or the inner or middle ear.

The term "follicules of the thyroid gland" as used herein relates to closed cavities filled with a colloid substance, constituting the lobules of the thyroid gland. "Synovium of the joint" as used herein refers to a membrane formed by synoviocytes found in the joints. The synovial membrane secretes synovial fluid which is found in the joint cavities, bursae and tendon sheaths. This fluid serves as a lubricant in the fluid spaces of the joint, i.e., joint cavities.

In particular, the terms "cells associated with the fluid spaces of the joint," "cells of the joint" and "structures comprising the joint" refer to all of the cellular and non-cellular materials which comprise the joint and are involved in the normal function of the joint or are present within the joint due to pathological conditions. These include material associated with: the joint capsule such as synovial membranes, synovial fluid, synovial cells (including type A cells and type B cells); the cartilaginous components of the joint such as chondrocytes, extracellular matrix of cartilage; the bony structures such as bone, periosteum of bone, periosteal cells, osteoblasts, osteoclasts; the immunological components such as inflammatory cells, lymphocytes, mast cells, monocytes, eosinophils; other cells like fibroblasts; and combinations of the above.

The "vitreous of the eye" as used herein refers to material that fills the chamber behind the lens of the eye (i.e., vitreous humor or vitreous body). Tissues comprising the eye include but are not limited to the cornea, lens, vitreous membrane, optic nerve, retina, supporting structure of the retinal, blood vessels of the eye, the cornea and the optic muscles. The "inner ear" refers to the labyrinth which includes the vestibule, cochlea and semicircular canals. The "middle ear" refers to the space in the temporal bone containing the auditory ossicles, i.e., tympanic cavity. Tissues comprising the middle or inner ear include but are not limited to the myelin sheath, fascia, sensory (auditory) neurons, neural derived hair cells, spiral ligament, stria vascularis, basilar membrane, semicircular canal, utricle, endolymphatic duct, saccule, middle ear cleft, scala vestibuli, scala tympani, scala media, tunnel of corti, auditory and vestibular nerves, inner and outer hair cells, basement membrane, tectorial membrane, Deiter's cells, Hensen's cells, claudius'cells, Boettcher's cells, fibrous tissue, perilymph and endolymph.

As used herein, a cell associated with the fluid space refers to cells in close proximity to the fluid space. Cells associated with fluid spaces are those which are in contact with the fluid without separation by a continuous cellular or basement membrane barrier. This would include but is not limited to those cells referenced above.

The term "vector," "DNA vector" or "DNA expression vector" as used herein refers to a nucleic acid, e.g., DNA derived from a plasmid, cosmid, phasmid or bacteriophage or synthetically derived, into which fragments of nucleic acid may be inserted or cloned. The vector can contain one or more unique restriction sites for this purpose, and may be capable of autonomous replication in a defined host or organism such that the cloned sequence is reproduced. The vector molecule can confer some well-defined phenotype on the host organism which is either selectable or readily detected. Some components of a vector may be a DNA molecule incorporating: sequences encoding a therapeutic or desired product; regulatory elements for transcription, translation, RNA stability and replication; and other DNA sequences.

The term "formulated DNA expression vector" as used herein refers to purified DNA vectors or DNA vectors associated with formulation elements useful for introduction and administration of the DNA vector into a cell such as lipids, proteins, carbohydrates, synthetic organic compounds, or in-organic compounds. Examples of formulation elements include, but are not limited to, lipids capable of forming liposomes, cationic lipids, hydrophilic polymers, polycations (e.g. protamine, polybrine, spermidine, polylysine), peptide or synthetic ligands recognizing receptors on the surface of the target cells, peptide or synthetic ligands capable of inducing endosomal-lysis, peptide or synthetic ligands capable of targeting materials to the nucleus, gels, slow release matrices, soluble or insoluble particles, as well as other formulation elements not listed. This includes formulation elements disclosed below for enhancing the delivery, uptake, stability, and/or expression of genetic material into cells.

The term "vector" as used herein does not include viral vectors. A "viral vector" in this sense is one that is physically incorporated in a viral particle by the inclusion of a portion of a viral genome within the vector, e.g., a packaging signal, and is not merely DNA or a located gene taken from a portion of a viral nucleic acid. Thus, while a portion of a viral genome can be present in a vector of the present invention, that portion does not cause incorporation of the vector into a viral particle and thus is unable to produce an infective viral particle.

A vector as used herein can also include elements which enable extra-chromosomal (episomal) replication of DNA. Vectors capable of episomal replication are maintained as extra-chromosomal material and can replicate. These sequences are not eliminated by simple degradation but continue to be copied. These sequences may be derived from a viral genome. These provide prolonged or "persistent" expression as described below.

The purpose of the formulated DNA expression vector is for expression of a nucleic acid sequence in a cell associated with a fluid space. Expression includes the efficient transcription of an inserted gene or nucleic acid sequence within the vector. Expression products may be proteins (including but not limited to proteins, glycoproteins, lipoproteins, phosphoproteins, etc.) or RNA. The gene insert or nucleic acid sequence is contained in the nucleic acid cassette.

Cells associated with fluid spaces incorporate the formulated DNA expression vector into the cell. "Incorporate" refers to uptake or transfer of the formulated DNA expression vector into a cell such that the formulated DNA expression vector can express the therapeutic gene product within the cell. Significantly, incorporation may involve, but does not require integration of the DNA expression vector or episomal replication of the DNA expression vector. Incorporation in this sense includes the short term persistence of the DNA expression vector in the cell before it is eliminated by degradation or translocation to other compartments.

Incorporation includes expression of the nucleic acid cassette by cells, whether it is transient expression persistent expression or stable expression. "Transient expression" as used herein relates to the introduction of genetic material into a cell to express specific proteins, peptides or RNA, etc. The introduced genetic material is not integrated into the host cell genome, or replicated and is accordingly eliminated from the cell over a period of time by degradation or translocation to other compartments.

"Persistent expression" as used herein refers to introduction of genes into the cell together with genetic elements which enable episomal (i.e., extrachromosomal) replication. This can lead to apparently stable transformation of the cell without the integration of the novel genetic material into the chromosome of the host cell.

"Stable expression" as used herein relates to the introduction of genetic material into chromosomes of the targeted cell where it integrates and becomes a permanent component of the genetic material in that cell. Gene expression after stable introduction can permanently alter the characteristics of the cell and its progeny arising by replication leading to stable transformation.

The term "nucleic acid cassette" as used herein refers to genetic sequences within the vector which can express a protein or RNA. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end.

A variety of proteins can be encoded by the sequence in a nucleic acid cassette in the transformed cells. These proteins can be post-translationally modified to be proteins, glycoproteins, lipoproteins, phosphoproteins, etc. Those proteins which can be expressed may function as intracellular or extracellular structural elements, ligands, hormones, neurotransmitters, growth regulating factors, enzymes, serum proteins, receptors, carriers for small molecular weight compounds, drugs, immunomodulators, oncogenes, tumor suppressors, toxins, tumor antigens. These proteins may have a natural sequence or a mutated sequence to enhance, inhibit, regulate, or eliminate their biological activity.

Specific examples of these compounds include extracellular matrix proteins, collagens, cytoskeletal proteins, cytokines including IL-1, IL-4, IL-6, IL-8, IL-10, IL-1 receptor antagonist, a soluble IL-1 receptor, complement proteins, growth factors including insulin, p53, SDJ, RL growth inhibitors, IGF-1, IGF-2, EGF, NGF, PDGF, ciliary nerve growth factor, FGF, TGF-α, TGF-β, interferons (α, β, γ), p53, Rb, or SDI, transplantation antigens, histocompatibility antigens (including class I and II transplantation antigen), allogeneic transplantation antigen, xenogeneic transplantation antigens, bacterial antigens, parasitic antigens, viral antigens, cell adhesion antigen, tumor specific antigens, receptors for natural ligands, receptors for drugs, genetically modified receptors for natural ligands, steroid receptors, genetically modified steroid receptors, receptors for angiostatic steroids, enzymes of prostaglandin metabolism, enzymes for collagen and extracellular matrix degradation including metalloproteinases, enzymes for synthesis and secretion of synovial fluid, vitreous fluid, or fluid of inner ear, enzymes for thyroid hormone synthesis, receptors for peptide backbones for peptidoglycan, receptors for platelet Factor 4, receptors for angiogenesis modulator factors, hormones including somatotropin, thyrotropin, prolactin, endorphin, thyroglobulin, thyroid peroxidase, and serum proteins such as clotting factors (VIII, IX, VII).

In addition, the nucleic acid cassette can encode a "transforming gene" which encompasses viral oncogenes, endogenous proto-oncogenes and activated proto-oncogenes or inhibitors of such transforming genes. A variety of oncogenes are known in the art. The term "oncogene" means those genes which cause cancer and include both viral and cellular oncogenes, many of which are homologous to DNA sequences endogenous to rodents and/or humans. The term "oncogene" includes both the viral sequence and the homologous endogenous sequences. Some examples of transforming genes are Ha-ras, Ki-ras, N-ras, fos, myc, src, sis, erbA, erbB, jun, HPV E7, HPV E6, HPV E5, Rb, p53, WT1, TGF-α, TGF-β, EGFR.

The RNA may function as a template for translation, as an antisense inhibitor of gene expression, as a triple-strand forming inhibitor of gene expression, as an enzyme (ribozyme) or as a ligand recognizing specific structural determinants on cellular structures for the purpose of modifying their activity. Specific examples include RNA molecules to inhibit the expression or function of prostaglandin synthase, lipooxygenase, histocompatibility antigens (class I or class II), cell adhesion molecules, nitrous oxide synthase, $\beta_2$ macroglobulin, oncogenes, and growth factors.

Another important embodiment of the present invention is a novel application of genetically modified receptors for regulating expression of recombinant gene products as disclosed in U.S. Pat. application, Ser. No. 07/882,771, entitled "Mutated Steroid Hormone Receptors and Methods for Their Use", O'Malley et al., filed May 14, 1992, and hereby incorporated by reference (including drawings). O'Malley et al., describe modified receptors expressed by formulated DNA expression vectors to control the level of expression of recombinant gene products. The steroid receptor family of gene regulatory proteins is an ideal set of such molecules. These proteins are ligand activated transcription factors whose ligands can range from steroids to retinoids, fatty acids, vitamins, thyroid hormones and other presently unidentified small molecules. These compounds bind to receptors and either up-regulate or down-regulate transcription.

These receptors are modified to allow them to bind various ligands whose structure is either naturally occurring or differs from naturally occurring ligands. For example, small C-terminal alterations in amino acid sequence of the receptor, including truncation, result in altered affinity and altered function of the ligand. Likewise the ligand can be altered as well. By screening receptor mutants, receptors can be customized to respond to ligands which do not activate the host cells own receptors. Thus, regulation of a desired transgene can be achieved using a ligand which will bind to and regulate a customized receptor. This would occur only with cells that have incorporated expressed the modified receptor.

In particular, an embodiment of the present invention includes using a modified steroid receptor which includes a modified steroid receptor DNA binding domain derived from the glucocorticoid receptors attached to a modified ligand binding domain on the receptor which is activated by a novel ligand and not by natural or synthetic glucocorticoids or other natural or synthetic steroids. This modified receptor is introduced into cells using formulated DNA expression vectors and methods described in this invention. The modified steroid receptor contains a DNA binding domain derived from the glucocorticoid receptor and produces a biological or therapeutic response in the target tissue similar to that produced by the administration of a glucocorticoid such as cortisone, hydrocortisone, dexamethasone, or prednisone, in response to a novel ligand. The novel ligand has a corticosteroid-like effect only on cells expressing the modified receptor, and is selected to have less systemic toxicity than natural corticosteroids. In another embodiment, a modified glucocorticoid receptor is introduced into cells which are continually on or active even in the absence of a ligand.

The term "flanking region" as used herein refers to nucleotide sequences on either side of an associated gene. Flanking regions can be either 3' or 5' to a particular gene in question. In general, flanking sequences contain elements necessary for regulation of expression of a particular gene. Flanking regions can include regulatory sequences necessary for tissue-specific expression, differentiation-specific expression, as well as sequences necessary for efficient expression.

Usually, specific regulatory sequences or elements are embedded adjacent to or within the protein coding regions of DNA. These elements, located adjacent to the gene in the 5' flanking region, 3' flanking region, or introns of the gene, are termed cis-acting elements. The signals are recognized by other biomolecules in trans to potentiate the transcriptional activity. These biomolecules are termed "trans-acting factors". The presence of the trans-acting factors and cis-acting elements have been shown to contribute to the timing, regulation, and developmental expression pattern of a gene.

The 5' flanking regions may include a promoter, a TATA box, a CAP site and a first intron and intron/exon boundary which are in an appropriate relationship sequentially and positionally for the expression of an associated gene. In this invention, "necessary sequences" are those elements of the 5' flanking region which are sequentially and positionally in an appropriate relationship to cause the specific expression of a nucleic acid cassette. The 5' flanking region can also provide tissue-specific expression to an associated gene.

The 5' flanking region is located 5' to the associated gene or nucleic acid sequence to be expressed. The 5' flanking region can be defined by known procedures. For example, the active portion of the 5' flanking region can be mapped by mutational analysis or various clones created to define the desired activity in a selected vector.

The term "promoter" as used herein refers to a recognition site of a DNA strand to which the RNA polymerase binds. The promoter forms an initiation complex with RNA polymerase to initiate and drive transcriptional activity. The complex can be modified by activating sequences termed "enhancers" or inhibitory sequences termed "silencers".

The promoter can be one which is naturally (i.e., as it occurs with a cell in vivo) or non-naturally associated ith the 5' flanking region of a particular gene. Promoters can be derived from eukaryotic genomes, viral genomes, or synthetic sequences. Promoters can be selected to be non-specific (active in all tissues), tissue specific, regulated by natural regulatory processes, regulated by exogenously applied drugs, or regulated by specific physiological states such as those promoters which are activated during an acute phase response or those which are activated only in replicating cells. Non-limiting examples of promoters in the present invention include the retroviral LTR promoter, cytomegalovirus immediate early promoter, SV40 promoter, dihydrofolate reductase promoter. The promoter can also be selected from those shown to specifically express in the select cell types which may be found associated with the structures of the: (1) joint such as synovial cells, fibroblasts, lymphocytes, periosteal cells, chondrocytes, osteoblasts, osteoclasts; (2) thyroid, such as folliculocytes; (3) eye; (4) middle or inner ear; (5) combinations of the above cell types. Examples of such promoters include but are not limited to the thyrotropin receptor promoter, insulin promoter, thyroid peroxidase promoter, malate dehydrogenase promoter, class I histocompatibility antigen promoter, thyroglobulin promoter, metalloproteinase promoters, and collagen promoters.

One skilled in the art will recognize that the selection of the promoter will depend on the vector, the nucleic acid cassette, the cell type to be targeted, and the desired biological effect. One skilled in the art will also recognize that in the selection of a promoter the parameters can include: achieving sufficiently high levels of gene expression to achieve a physiological effect; maintaining a critical level of gene expression; achieving temporal regulation of gene expression; achieving cell type specific expression; achieving pharmacological, endocrine, paracrine, or autocrine regulation of gene expression; and preventing inappropriate or undesirable levels of expression. Any given set of selection requirements will depend on the conditions but can be readily determined once the specific requirements are determined. Those promoters which naturally occur in the cells comprising the thyroid, ear, eye, and structures of the joint, and restrict expression to these sites will be preferred.

The term "intron" as used herein refers to a section of DNA occurring in a transcribed portion of a gene which does not code for an amino acid in the gene product. RNA transcribed by RNA polymerase as it reads through the intron is included in a precursor RNA, and is then excised so that it is not present in the mature messenger RNA nor translated into protein. The term "exon" as used herein refers to a portion of a gene that is included in the transcript of a gene and survives processing of the RNA in the cell to become part of a messenger RNA (mRNA). The intron/exon boundary will be that portion in a particular gene where an intron section connects to an exon position. The terms "TATA box" and "CAP site" are used as they are recognized in the art.

The 3' flanking region can contain sequences which contribute to regulation of expression of a nucleic acid sequence. The 3' flanking regions can also enhance tissue-specific expression of an associated gene. In addition, the 3' flanking region may also encode sequences for mRNA stability. The 3' flanking region can be included within a vector of this invention 3' to that of an associated gene in order to regulate its expression. The term as used herein includes that portion of the naturally occurring 3' flanking region with effects on the expression of the nucleic acid cassette. That portion can be readily defined by known procedures. For example, the active portions of a 3' flanking region can be mapped by mutational analysis or various clones created to define the desired activity in a selected vector system.

The 3' flanking region can contain a 3' untranslated region (3' UTR). This term refers to the sequence at the 3' end of a structural gene which is usually transcribed with the gene. This 3' UTR region of an mRNA encoding a protean usually contains a poly(A) sequence. Although the 3' UTR is transcribed from the DNA, it is not translated into protein. Specific 3' UTR sequences may be used to allow for specific mRNA stability with a cell. The term "mRNA stability" as used herein refers to the rate of metabolic breakdown or decay of an mRNA molecule within a cell. The faster the turnover (i.e., breakdown) of mRNA the less stable the mRNA is within a cell. In contrast, the slower the turnover of an mRNA, the more stable the mRNA is within a cell. Such stability correlates directly with the rate of expression of a given gene, i.e., synthesis of the corresponding protein. These decay rates of individual mRNA species directly affects the duration of activity therapeutic product transiently expressed in a cell. These decay rates also directly affect the steady state expression levels of a gene which is persistently or stably incorporated in a cell, i.e., increased stability causes increase in expression.

The 3' flanking region can also contain a 3' noncoding region (3' NCR). The 3' NCR is a region contiguous to the 3' UTR region of a structural gene. The 3' NCR region generally contains a transcriptional termination signal. In addition to the 3' UTR, the 3' UTR and 3' NCR sequences together can provide a higher level of mRNA accumulation through increased mRNA stability.

The 3' UTR and 3' NCR can be selected and incorporated into the vector to specifically enhance the level and duration of expression of a therapeutic product expressed from a formulated DNA expression vector and delivered to tissues by the methods described herein. Specifically, these elements are selected to maintain the level of the therapeutic gene product within the range of its safe, therapeutic effect.

The term "linker" as used herein refers to DNA which contains the recognition site for a specific restriction endonuclease. Linkers may be connected to the ends of DNA fragments prepared by cleavage with some other enzyme. A linker having a unique restriction endonuclease site at the location of the start and stop codon connects the 5' flanking region to a nucleic acid. In particular, the linker provides a position for inserting the nucleic acid cassette which contains a specific nucleic acid sequence to be expressed. This position may be an endonuclease site in the linker, such as ClaI, NotI, XmaI, BglII, PacI, XhoI, NheI and SfiI.

One skilled in the art will readily recognize that certain elements of the above described vector may be eliminated for specific applications.

The vector can also be introduced with a formulation for facilitating incorporation of the vector into the cell. The term "formulation" as used herein refers to non-genetic material combined with the vector in a solution, suspension, or colloid which enhances the delivery, uptake, stability, and/or expression of genetic material by the cell. By "formulation" the present invention specifically describes particles containing DNA expression vectors which are capable of extravescating into fluid spaces. In a preferred embodiment of the present invention these particles are nanoparticles. In a preferred embodiment of the present invention the formulation comprises a suspension or colloid. The formulation can include lipids, proteins, carbohydrates, synthetic organic compounds, or in-organic compounds. Examples of such formulation elements include, but are not limited to, lipids capable of forming liposomes, cationic lipids, hydrophilic polymers, polycations (e.g. protamine, polybrine, spermidine, polylysine), peptide or synthetic ligands recognizing receptors on the surface of the target cells, peptide or synthetic ligands capable of inducing endosomal-lysis, peptide or synthetic ligands capable of targeting materials to the nucleus, gels, slow release matrices, soluble or insoluble particles. The material to be used in a formulation in the present invention can also include but is not limited to lactoferrin, histones, natural or synthetic DNA binding proteins, natural or synthetic DNA binding compounds, viral proteins, nonviral proteins or any combination of these. In addition, the formulation may be comprised of synthetic compounds which bind both to DNA and function as ligands for receptors on cells comprising the thyroid, ear, eye, or structures of the joint.

For the thyroid, proteins having natural tropism to the thyroid including thyrotropin (TSH), thyroglobulin, monoclonal/polyclonal antibodies, and thyroid-specific antigens can be used. Binding of these complexes, coupled to the vector, leads to uptake and expression of the vector in the thyroid.

Gene therapy by the above method is in vivo. In one embodiment, formulated DNA expression vectors of the present invention are directly injected into the fluid spaces so that cells associated with the fluid spaces (e.g., synoviocytes, thyroid follicles, or cells associated with the eye or ear) incorporate the vector.

In another embodiment, in vivo introduction of a vector into thyroid folliculocytes for gene transfer and therapy can include the steps of administering a vector complexed with a protein into blood. The protein is capable of binding the receptors on the thyroid. The protein is usually selected from the group consisting of thyrotropin, thyroglobulin, thyroid binding poly-antibody and thyroid binding monoclonal-antibody. By the complexing of this protein with the vector, the vector is targeted to the thyroid gland.

An additional embodiment for the in vivo introduction of a DNA vector into thyroid folliculocytes comprises the step of administration of a vector combined with ballistic particles. The particles are selected from the group consisting of particles bound to DNA or particles for slow release of DNA. An example of this is the gene gun of DuPont®. Yang et al., Proc. Natl. Acad. Sci. USA 87:9568–72, 1990.

An additional embodiment for the in vivo introduction of a DNA vector into joints comprises the step of administration of a particle containing the DNA-expression vector that extravescates from the vascular space into the joint space due to the damage to this joint associated with arthritis.

A second aspect of the present invention features methods for transforming a cell associated with the fluid space. This method comprises the steps of introducing a vector into the fluid space and contacting the cell with the vector for sufficient amount of time to transfect the cell. The term "transfection" as used herein refers to the process of introducing DNA (e.g., formulated DNA expression vector) into a cell. Following entry into the cell, the transfected DNA may: (1) recombine with that of the host; (2) replicate independently as a plasmid or temperate phage; or (3) be maintained as an episome without replication prior to elimination. Cells may be naturally able to uptake DNA. Particular cells which are not naturally able to uptake DNA require various treatments, as described above, in order to induce the transfer of DNA across the cell membrane.

As used herein, "transformation" relates to transient or permanent changes in the characteristics (expressed phenotype) of a cell induced by the uptake of a vector by that cell. Genetic material is introduced into a cell in a form where it expresses a specific gene product or alters the expression or effect of endogenous gene products.

Transformation is performed by in vivo techniques as described below. Transformation of the cell may be associated with production of a variety of gene products including protein and RNA. These products may function as intracellular or extracellular structural elements, ligands, hormones, neurotransmitters, growth regulating factors, enzymes, serum proteins, receptors, carriers for small molecular weight compounds, drugs, immunomodulators, oncogenes, tumor suppressors, toxins, tumor antigens, antigens, antisense inhibitors, triple strand forming inhibitors, ribozymes, or as a ligand recognizing specific structural determinants on cellular structures for the purpose of modifying their activity. Other examples can be found above in the discussion of nucleic acid cassette. The product expressed by the transformed cell depends on the nucleic acid of the nucleic acid cassette. This list is only an example and is not meant to be limiting.

One embodiment of the present invention is a transformed synovial cell, thyroid folliculocyte, or cells associated with the eye or ear, comprised of nucleic acid incorporated into the cell by gene transfer. In specific embodiments, the nucleic acid can be any of the genetic materials described above. Transformed cells are capable of expressing either proteins or RNA.

A third related aspect of the present invention features a cell associated with a fluid space transformed with a vector as described above for the expression of a nucleic acid sequence. As described above, the nucleic acid cassette may contain genetic material encoding for a variety of proteins or RNA. That cell may be associated with a fluid space selected from or created by the group consisting of the follicles of the thyroid, the synovium of the joint, the vitreous of the eye and the inner or middle ear.

A fourth related aspect of the invention features an animal model whose cells associated with a fluid space contain the formulated DNA expression vector referenced above. This animal model can be used to model the pathogenesis of disease. Animal models can be used to assess and explore novel therapeutic avenues.

In a fifth related aspect, the invention features a method for inducing an immune or immunological response by transforming a cell associated with a fluid space with the above-referenced vector. The nucleic acid cassette may contain nucleic acid sequences coding for proteins or polypeptides or other factors which might produce an immunogenic or immunological response. The nucleic acid cassette can contain genetic material that encodes for microbial antigens including bacterial antigens, viral antigens, and parasitic antigens. Examples include genetic material coding for a viral capsid protein from the human papilloma virus, other viral capsids, bacterial protein and toxins. An immune response may also be generated by expressing cytokines including IL-1, IL-6, or γ-interferon. This is only an example and is not meant to be limiting.

A sixth related aspect of the present invention features a method for ablation (i.e., cell destruction) of inflammatory cells in a joint by introducing a vector as described above, into a fluid space associated with the joint. The vector is also targeted for selective uptake of phagocytic cells. The vector contains in the 5' flanking region necessary sequences for specific expression of nucleic acid cassettes in leukocytes within the joint. This can include a promoter which regulates expression of a nucleic acid cassette specifically in leukocytes. The vector can be introduced into the fluid space with a formulation, as described above, which facilitates uptake of the vector by the phagocytic cell.

The nucleic acid cassette in the above vector can encode for an ablation agent. The term "ablation agent" as used herein refers to an agent which is capable of destroying the cell in which it is present by a cytotoxic effect or apoptosis. Examples of ablation agents used in the present invention include diphtheria toxin, nitrous oxide synthase and herpes thymidine kinase. In an additional embodiment, the vector is directly targeted to certain immune cells (e.g. T-cells) by attaching the vector to a molecule which attaches to the surface of the phagocytic cell, e.g., an antibody or ligand specific to a surface antigen such as CD4, CD8, or the IL-2 receptor. This is only an example and is not meant to be limiting.

In a seventh aspect, the present invention features methods for treating diseases associated with the group selected from the joints, thyroid, ear and eye. This method comprises the steps of introducing a vector into a fluid space so that cells associated with the fluid space incorporate the vector into the cell.

Introduction of a formulated DNA expression vector into cells comprising the thyroid, eye, ear or structures of the joint can be used to treat a variety of pathological conditions. The disease is first diagnosed and the appropriate vector administered to treat the diagnosed disease. These conditions can result from: the abnormal production of a protein, for example too little or too much of a protein; the production of an abnormal protein; atopic production of a protein; or abnormal regulation of production of a protein. Introduction of a vector into cells can also be used to provide proteins or peptides or genetic elements (DNA or RNA) with therapeutic actions. One skilled in the art will recognize that even complex pathophysiological events such as inflammatory diseases, degenerative, diseases, injury and regeneration can be understood as comprising a series of molecular interactions between proteins and can be treated according to the embodiment of this invention.

With respect to the joints, diseases which can be treated by the methods of the present invention include those diseases known to one in the art as arthritis. This includes pathophysiological conditions resulting from inflammatory processes; hypertrophy or inappropriate proliferation of cellular elements of the joint; damage to the joint; enhancement of repair, regeneration, and recovery of essential structures comprising the joint after surgery or injury; and other acquired diseases of the joints. For example, in the treatment of a pathological condition the vector with or without a formulation will be introduced into cells comprising structures of the joint- by injecting a pharmacological dose of the vector with or without a formulation into a joint. The nucleic acid cassette in the vector encodes a protein, polypeptide or RNA. The vector is taken up by appropriate cells within the joint and expresses the protein, polypeptide or RNA. The preferred embodiment of this invention involves transient or persistent expression within the joint. This is preferable to stable expression since it enables adjustment of the level of expression in response to the evolution of the disease process.

Specific diseases which can be treated by administration of vectors to cells within the joint include various arthritises, avascular necrosis, or injuries requiring repair and regeneration of structures comprising the joint. The various types of arthritis which can be treated, include but are not limited to: tendinitis; bursitis; fibrositis; bone lesions; soft tissue inflammation; degenerative joint disease; traumatic disorders; neuropathic arthropathy; metabolic disorders; synovial tumors; pigmented villonodular synovitis; hemorrhagic disorders; septic disorders; crystal induced disorders (gout); immune complex disease and vasculitis; systemic lupus erythematosus; rheumatoid arthritis; Reiter's syndrome; psoriasis; ankylosing spondylitis; scleroderma; and arthritis of intestinal disease. In specific embodiments of the present invention for the treatment of arthritis, a soluble receptor for cytokines can be used. Examples of a soluble receptor include receptor for IL-1 or IL-6. In specific embodiments of the present invention, an anti-inflammatory cytokine may be expressed including IL-4, IL-10, or TGF-$\beta$.

An alternative embodiment of the present invention includes a method of treating arthritis in humans comprising the step of injecting an inflamed joint of a human with a pharmacological dose of a DNA vector in a formulation, wherein the nucleic acid cassette in the vector encodes a sequence for a steroid receptor for a natural or synthetic steroid ligand. This can be the normal receptor or it can be a genetically modified receptor as described above, e.g. the glucocortico-mimetic receptor.

When treating pathophysiological conditions or repairing or regenerating structures of the joint, it is found that a useful nucleic acid cassette encodes an RNA inhibitor of prostaglandin synthase, lipoxegenase or other enzymes involved in prostaglandin synthesis. These enzymes are known to those skilled in the art as targets for non-steroidal, anti-inflammatory drugs such as aspirin.

Another embodiment of the present invention is a method of targeting vectors to joints comprising the steps of identifying human antibodies from patients with autoimmune arthritis, cloning the antibodies to develop monoclonals with the same epitope binding determinants, coupling vectors of the present invention to the monoclonals, and constructing particles containing the DNA vector capable of extravescating into the inflamed joint. By this method, the formulated vector is delivered to the cells of the joint. One skilled in the art recognizes that a variety of methods are available for identifying antibodies.

Gene transfer to the thyroid can be used for therapeutic purposes including the provision of normal serum proteins to replace genetically defective proteins, the constitution of regulated expression of select hormones which were deficient because of inherited or acquired diseases, the replacement of essential biological functions in the thyroid which prevent the normal synthesis of thyroid hormone, the secretion of novel proteins into the blood for therapeutic purposes, or the secretion of peptides with neurotropic function.

In the alternative case, where there is not enough protein being produced, thyroid folliculocytes transformed with the vector capable of expressing normal protein can be used to produce sufficient quantity of the protein. Further, transformed thyroid folliculocytes capable of expressing regulatory protein co-factors, receptors or other factors can also be used to increase or decrease production. One skilled in the art will readily recognize that the ability of thyroid folliculocytes to produce a protein or RNA can be measured by standard conditions both in vivo and ex vivo.

Another method of treating pathophysiological conditions is the replacement of an abnormal protein or polypeptide with a normal protein. Again, a protein or an antisense RNA can be introduced to stop the production of the abnormal protein. Further, the normal sequence can be introduced to result in the production of the normal counterpart.

Certain pathophysiological conditions regarding the thyroid which can be treated include protein deficiency, glycoprotein deficiency, hormone deficiency, immune deficiency, clotting factor deficiency and autoimmune disease. Specific disease which can be treated by transformed folliculocytes include diabetes mellitus, hypothyroidism, hyperthyroidism, hemophilia and immune complement deficiency. In addition, diseases or other undesirable conditions which result from surgery, injury, infection, pharmacological therapy, radiation therapy, chronic diseases and aging can also be treated by using transformed thyroid folliculocytes.

Gene transfer to the ear using the methods of the present invention can be utilized to treat congenital, acquired, or degenerative causes of deafness. In particular, one embodiment of the present invention is use of the above vectors to treat inflammation or other dysfunctions of the vestibular system. Vectors encoding for expression factors capable of inducing regeneration, reinnervation, repair, growth or revascularization of essential structures including nerves.

Gene therapy using the present methods can be utilized to treat congenital, acquired or degenerative causes of blindness or visual deficit. Vectors can be constructed to express genes which enhance the growth, regeneration, repair, or function of the optic nerve and retinal tissues and to increase or decrease inappropriate vascularization of the retina. This includes photoreceptors and nerves that have been damaged or are deteriorating as a result of aging, infection, trauma, surgery, abnormal vascularization or other systemic disorders. In particular, gene therapy by the present invention include, but is not limited to the treatment of: genetic defects of vision; glaucoma; cataracts; inflammatory disorders of the eye, cornea, retinal, conjunctiva, tear ducts, or sclera; neovascularization within the eye; strabismus; diabetes; amblyopia; and defects of accommodation associated with aging or injury.

The genetic material which is incorporated into the cells associated with fluid spaces from the above vectors includes: (1) nucleic acid not normally found in the cells; (2) nucleic acid which is normally found in the cells but not expressed at physiological significant levels; (3) nucleic acid normally found in the cells and normally expressed at physiological desired levels; (4) other nucleic acids which can be modified for expression in the cells; and (5) any combination of the above.

The vectors of the above methods may be administered by various routes. The term "administration" refers to the route of introduction of a formulated vector into the body. Administration may be intravenous, intramuscular, topical, oral, or by gene gun or hypospray instrumentation. Administration can be directly to a target tissue or through systemic delivery. In the preferred embodiment, systemic delivery involves intravenous administration. Administration directly to the target tissue can involve needle injection, hypospray, electroporation, or the gene gun. See, e.g., WO 93/18759, hereby incorporated by reference herein. The preferred embodiment is by direct injection.

One skilled in the art will readily recognize that a variety of other tissues, fluid space and extracellular spaces may be used. These include normal fluid spaces, potential spaces, cysts, spaces created by injury, infection, or congenital malformation, and sinuses. This list is included for exemplary purposes and is not intended to be limiting.

Other features and advantages of the invention will be apparent from the following detailed description of the invention in conjunction with the accompanying drawings and from the claims.

BRIEF DESCRIPTION OF THE DRAWINGS

FIG. 3 is a schematic of one proposed mechanism for targeting DNA to different cells such as chondrocytes and synovial cells.

FIG. 4 is a schematic representation of an ex vivo approach to gene therapy for delivery of genes to the thyroid.

FIG. 7 is a schematic representation of the structure of a retroviral vector for thyroid gene therapy.

FIG. 8 is a schematic representation of the structure of a nonviral vector for thyroid gene therapy.

FIG. 9 is a schematic representation of gene therapy applications for the thyroid.

Figure 1:
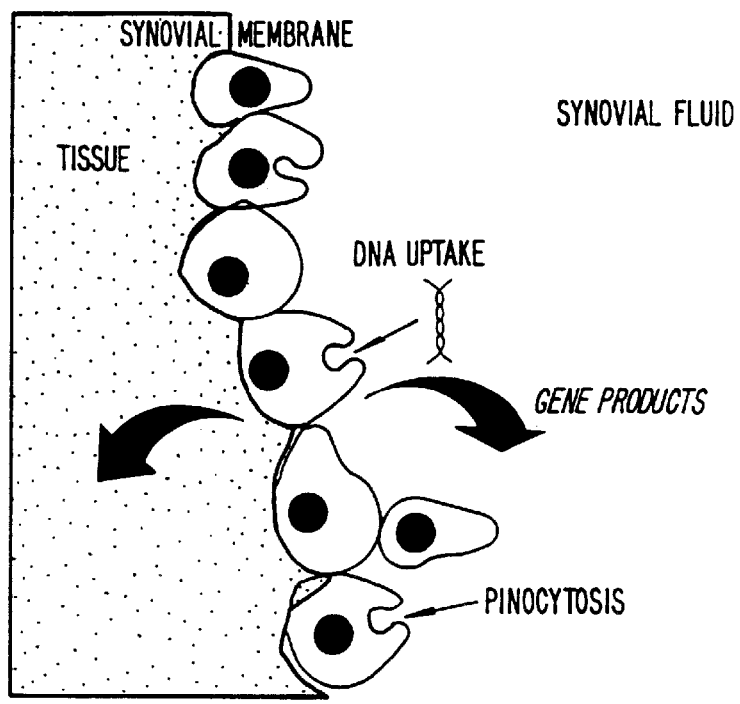
FIG. 1 is a schematic of one proposed mechanism for DNA mediated gene transfer into synovial cells.
Figure 2:
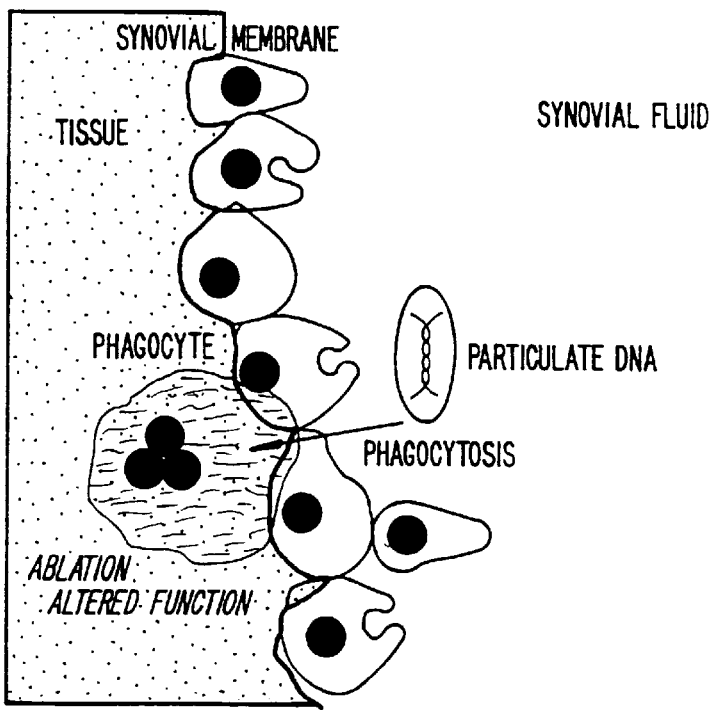
FIG. 2 is a schematic of one proposed mechanism for DNA mediated gene transfer into inflammatory cells invading the joint.
Figure 5:
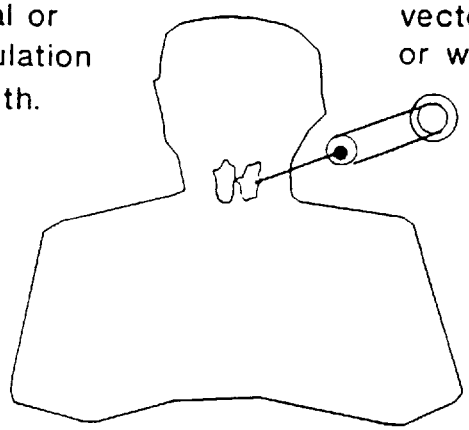
FIG. 5 is a schematic representation of an in vivo approach to thyroid gene therapy.
Figure 6:
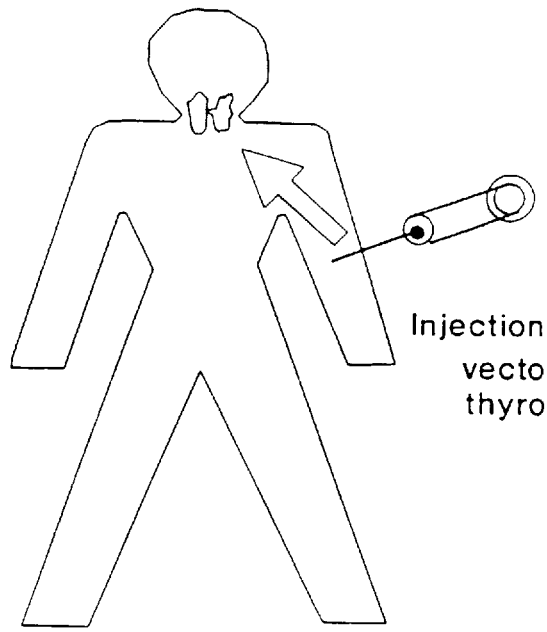
FIG. 6 is a schematic representation of an in vivo targeted thyroid gene therapy.

The drawings are not necessarily to scale and certain features of the invention may be exaggerated in scale and shown in schematic form in the interest of clarity and conciseness.

DETAILED DESCRIPTION OF THE INVENTION

The following are examples of the present invention in which genes are transferred to cells associated with fluid spaces by introducing formulated DNA expression vectors into the fluid spaces. The following are specific examples of preferred embodiments of the present invention. These examples demonstrate how formulated DNA expression vectors can be used to transfer therapeutic gene products to cells associated with fluid spaces in the joint, thyroid, ear and eye. Furthermore, it is demonstrated how to treat various diseases associated with the tissues above. The utility of such methods are noted herein and amplified upon in co-pending applications by Ledley, F. D. entitled "Targeting Somatic Gene Therapy to Joints," supra, and "Somatic Gene Therapy", supra, as well as co-pending application by Ledley, F. D. et al., entitled "Targeting Somatic Gene Therapy to the Thyroid", supra. Such sections are hereby specifically incorporated by reference herein.

It will be readily apparent to one skilled in the art that various substitutions and modifications may be made to the invention disclosed herein without departing from the scope and spirit of the invention.

Polymerase Chain Reaction (PCR) Detection of β-gal DNA Injected into the Knee of Rabbits CMV-β-gal vectors were constructed as described above with nucleic acid cassettes containing the β-gal gene. Vectors were combined with a formulation containing 20% sucrose at pH 7.4. This formulation was injected into the knee joints of rabbits using a transpatellar injection. In other experiments, addition, calcium phosphate precipitated DNA was injected. As controls, saline alone was injected. Three days after injection animals were sacrificed, the joint was disarticulated and the DNA extracted from the synovium. PCR amplified products from the DNA extract was visualized on autoradiogram. The analysis showed that CMV-β-gal DNA products was taken up and retained in the synovial tissue of rabbits injected with the above vectors. Experiments in rats produce equivalent results.

Introduction of a Marker Gene into Cells of the Joint

A vector comprising the cytomegalovirus immediate early promotor, 5' untranslated sequences and an intron from SV40, 3' untranslated sequences from SV40 including the polyadenylation signal and a nucleic acid cassette containing the E. coli β-galactosidase gene was combined with a formulation containing 20% sucrose at pH 7.4. This formulation was injected into the knee joint of rabbits using a transpatellar injection. As a control, an identical vector containing the E. coli chloramphenicol acetyltransferase gene in place of the β-galactosidase gene was injected into joints on the opposite leg using identical methods. Three days after injection animals were sacrificed, the joint was disarticulated, and stained in a formulation containing X-gal at pH 7.2. Under these conditions cells taking up and expressing the E. coli β-galactosidase gene will be stained blue. Cells not expressing β-galactosidase do not stain with this dye under these conditions.

The analysis showed that there was diffuse blue staining in regions of the joint representing the synovial cells of joint injected with the β-galactosidase containing vector. No staining was observed over the tendons of bony surfaces of the joints. No blue staining was apparent in joints injected with the control vector.

These results demonstrate that cells of the joint are capable of taking up DNA vectors and are capable of expressing gene products encoded by the vector. Experiments in rats produce equivalent results to those observed in rabbits.

Introduction of Human Growth Hormone into the Cells of Joints

Vectors were constructed as described above, except the nucleic acid cassette coded for human growth hormone. Vectors were combined with a formulation containing 20% sucrose at pH 7.4. This formulation was injected into the knee joint of two different rabbits using a transpatellar injection. As controls, identical vectors without the human growth hormone gene and pure saline were used. These were injected into different joints of the same rabbits. Three days after injection, the synovial fluid was withdrawn and analyzed for human growth hormone production.

Figure 10:
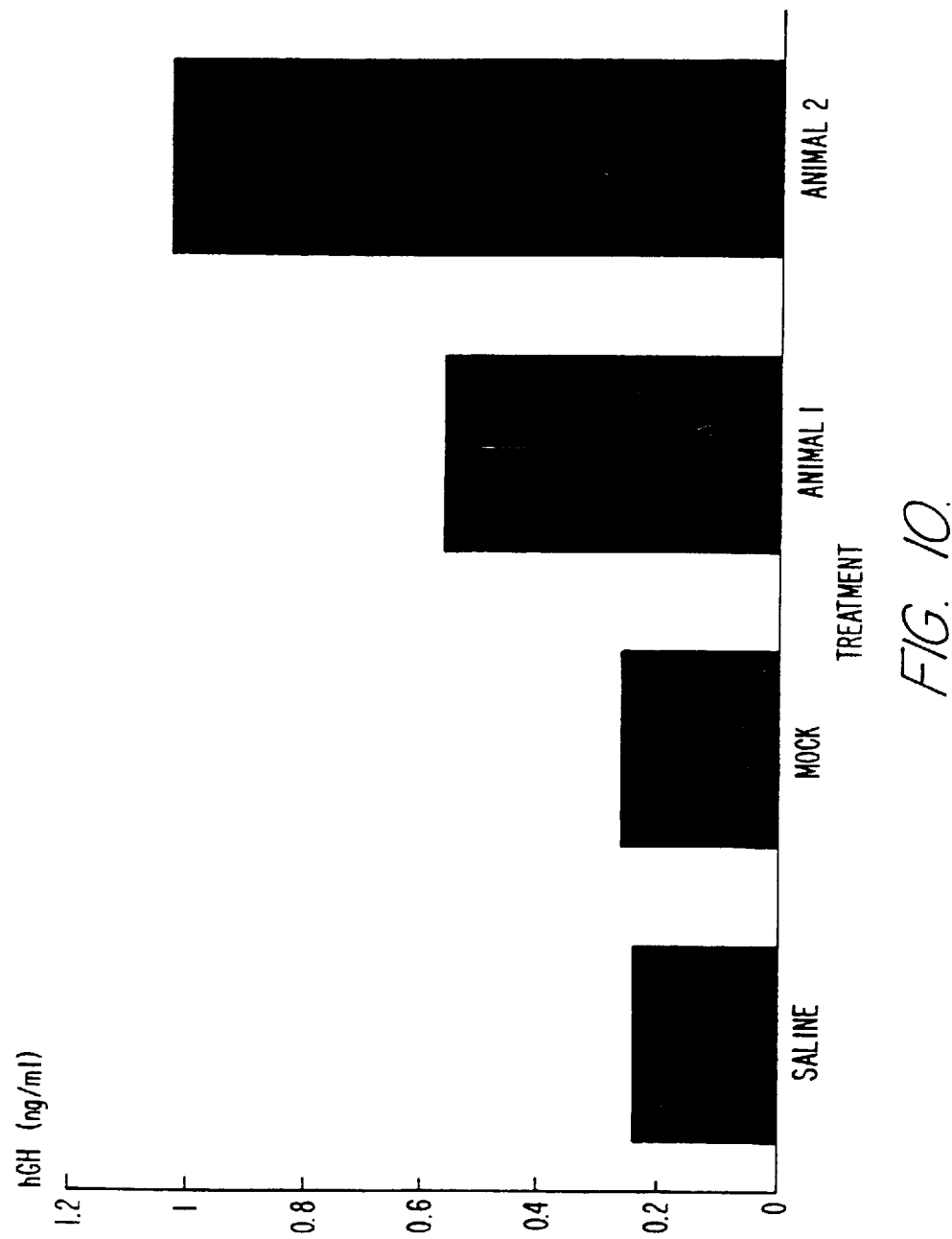
FIG. 10 represents the levels of growth hormone in synovial fluid after vector introduced into cells of the joints.

The analysis showed that cells taking up and expressing the DNA expression vector secreted human growth hormone into the synovial fluid (see FIG. 10). These results demonstrate further that cells of the joint are capable of taking up DNA vectors, expressing gene product encoded by the vectors and secreting the product into the fluid enclosed space.

CMV-CAT Plasmid Injected into the Knee of Rats

Figure 11:
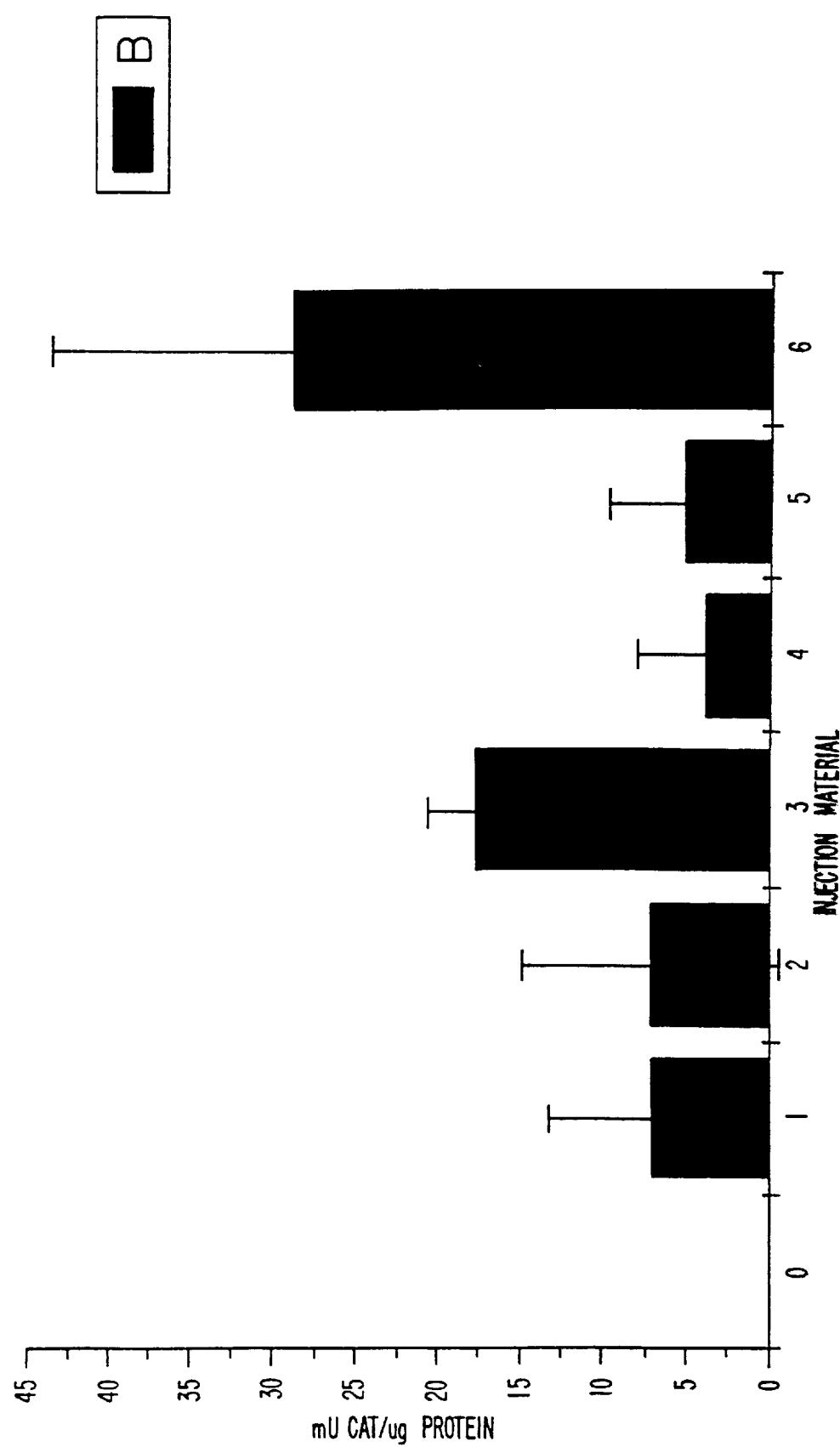
FIG. 11 is a representation of the activity of CAT in synovium of rats treated with a CMV-CAT plasmid.

CMV-CAT vectors were constructed as described above with nucleic acid cassettes containing the CAT gene. Vectors were combined with a formulation containing 20% sucrose at pH 7.4 (FIG. 11, lane 2). This formulation was injected into the knee joints of rats using a transpatellar injection. CMV-CAT vectors were also injected with PBS (lane 1); sucrose with localized mock PMA pretreatment (lane 3); sucrose with localized PMA pretreatment 30 minutes prior to injection (lane 4); sucrose with mock systemic dexamethasone treatment (lane 5); and sucrose with systemic dexamethasone treatment (lane 6). A control of no CAT DNA was also used. Three days after injection the animals were sacrificed and the synovium analyzed for CAT activity and the effect of auxiliary treatment with PMA or dexamethasone. The analysis showed CAT activity in the synovium of rats. FIG. 10, lane 6 represents approximately 6-fold increase in CAT expression with dexamethasone treatment. Lane 3 represents a 3-fold increase in CAT activity using mock PMA pretreatment over injection with PBS or sucrose and approximately a 4-fold increase over PMA pretreatment 30 minutes prior to injection.

These data demonstrate the utility of this method in another species. In addition, this demonstrates the utility of this method using an additional gene product.

Expression of Anti-Inflammatory Factors to Prevent Inflammatory Arthritis

The inflammatory attack on joints in animal models and human diseases may be mediated, in part, by secretion of cytokines such as IL-1 and IL-6 which stimulate the local inflammatory response. The inflammatory reaction may be modified by local secretion of soluble fragments of the receptors for these ligands. The complex between the ligand and the soluble receptor prevents the ligand from binding to the receptor which is normally resident on the surface of cells, thus preventing the stimulation of the inflammatory effect. Therapy consists of the construction of a vector containing the soluble form of receptors for appropriate cytokines (for example Il-1) together with promoters capable of inducing high level expression in structures of the joint and a formulation which enables efficient uptake of this vector. This DNA is injected into affected joints where the secretion of an inhibitor for IL-1 such as a soluble IL-1 receptor or natural IL-I inhibitor modifies the local inflammatory response and resulting arthritis.

This method is useful in treating episodes of arthritis which characterize many "autoimmune" or "collagen vascular" diseases. This method can also prevent disabling injury of large joints by inflammatory arthritis.

Induction of "Steroid Response" by Gene Transfer of Steroid Receptors into Cells of the Joint Current therapy for severe arthritis involves the administration of pharmacological agents including steroids to depress the inflammatory response. Steroids can be administered systemically or locally by direct injection into the joint space.

Steroids normally function by binding to receptors within the cytoplasm of cells. Formation of the steroid-receptor complex changes the structure of the receptor so that it becomes capable of translocating to the nucleus and binding to specific sequences within the genome of the cell and altering the expression of specific genes. Genetic modifications of the steroid receptor can be made which enable this receptor to bind naturally occurring steroids with higher affinity, bind non-natural, synthetic, steroids. Other modifications can be made to create steroid receptor which is "constitutively active" meaning that it is capable of binding to DNA and regulating gene expression in the absence of steroid in the same way that the natural steroid receptor regulates gene expression after treatment with natural or synthetic steroids.

Of particular importance is the effect of glucocorticoid steroids such as cortisone, hydrocortisone, prednisone, or dexamethasone which are the most important drugs available for the treatment of arthritis. One approach to treating arthritis is to introduce a vector in which the nucleic acid cassette expresses a genetically modified steroid receptor into cells of the joint, e.g. a genetically modified steroid receptor which mimics the effect of glucocorticoids but does not require the presence of glucocorticoids for effect. This is termed the glucocortico-mimetic receptor. This is achieved by expression of a constitutively active steroid receptor within cells of the joint which contains the DNA binding domain of a glucocorticoid receptor. This induces the therapeutic effects of steroids without the systemic toxicity of these drugs. Alternatively, steroid receptors which have a higher affinity for natural or synthetic glucocorticoids can be introduced into the joint. These receptors exert an increased anti-inflammatory effect when stimulated by non-toxic concentrations of steroids or lower doses of pharmacologically administered steroids. Alternatively, constitution of a steroid receptor which is activated by a novel, normally-inert steroid enables the use of drugs which would affect only cells taking up this receptor. These strategies obtain a therapeutic effect from steroids on arthritis without the profound systemic complications associated with these drugs. Of particular importance is the ability to target these genes differentially to specific cell types (for example synovial cells versus lymphocytes) to affect the activity of these cells.

As described in U.S. application Ser. No. 07/882,771, entitled "Mutated Steroid Hormone Receptors and Methods for Their Use", O'Malley et al., filed May 14, 1992, hereby incorporated by reference (including drawings), genetically modified receptors, such as the glucocortico-mimetic receptor, can be used to create novel steroid receptors including those with glucocortico-mimetic activity. The steroid receptor family of gene regulatory proteins is an ideal set of such molecules. These proteins are ligand activated transcription factors whose ligands can range from steroids to retinoids, fatty acids, vitamins, thyroid hormones and other presently unidentified small molecules. These compounds bind to receptors and either up-regulate or down-regulate transcription.

The preferred receptor of the present invention is modification of the glucocorticoid receptor, i.e., the glucocorticoid-mimetic receptor. These receptors can be modified to allow them to bind various ligands whose structure differs from naturally occurring ligands. For example, small C-terminal alterations in amino acid sequence, including truncation, result in altered affinity and altered function of the ligand. By screening receptor mutants, receptors can be customized to respond to ligands which do not activate the host cells own receptors.

A person having ordinary skill in the art will recognize, however, that various mutations, for example, a shorter deletion of carboxy terminal amino acids, will be necessary to create useful mutants of certain steroid hormone receptor proteins. Steroid hormone receptors which may be mutated are any of those receptors which comprise the steroid hormone receptor super family, such as receptors including the estrogen, progesterone, glucocorticoid-α, glucocorticoid-β, mineral corticoid, androgen, thyroid hormone, retinoic acid, and Vitamin B3 receptors.

Inhibition of Prostaglandin Synthase

Drugs which inhibit the enzyme prostaglandin synthase are important agents in the treatment of arthritis. This is due, in part, to the important role of certain prostaglandin in stimulating the local immune response. Salicylates are widely used drugs but can be administered in limited doses which are often inadequate for severe forms of arthritis.

Gene transfer is used to inhibit the action of prostaglandin synthase specifically in affected joints by the expression of an antisense RNA for prostaglandin synthase. The complex formed between the antisense RNA and mRNA for prostaglandin synthase interferes with the proper processing and translation of this mRNA and lowers the levels of this enzyme in treated cells. Alternatively RNA molecules are used for forming a triple helix in regulatory regions of genes expressing enzymes required for prostaglandin synthesis. Alternatively RNA molecules are identified which bind the active site of enzymes required for prostaglandin synthesis and inhibit this activity.

Alternatively, genes encoding enzymes which alter prostaglandin metabolism can be transferred into the joint. These have an important anti-inflammatory effect by altering the chemical composition or concentration of inflammatory prostaglandin.

Generating an Animal Model of Inflammatory Arthritis

Inflammatory arthritis is thought to result from an autoimmune attack on cells comprising essential structures of the joint. The association of various forms of arthritis with certain tissue transplantation (histocompatibility) antigens, suggests that these antigens, or dysregulation of these antigens, may play an important role in the genesis of these diseases.

Animal models of inflammatory arthritis can be generated by gene transfer of vectors capable of expressing heterogenic (not self) or xenogeneic (other species) transplantation antigens within the joint, thus mimicking the effect of dysregulation of tissue transplantation antigens. This induces an autoimmune attack not only on the transplantation antigens themselves, but on other antigens within the joint which are presented to the immune system in an abnormal manner.

Alternatively, overproduction of interferon in tissues is thought to induce dysregulation of class I antigens and potentiate a inflammatory reaction. This can be modeled in animals by introduction of vectors expressing γ-interferon into cells of the joint. Alternatively, the effect of cytokines in the pathogenesis of arthritis can be studied by expressing gene products such as IL-1, IL-6 or TNF within the joint.

Gene Transfer to Enhance Repair or Regeneration of Joints

The regenerative capacity of the joint is limited by the fact that chondrocytes are not capable of remodelling and repairing cartilaginous tissues such as tendons and cartilage. Further, collagen which is produced in response to injury is of a different type lacking the tensile strength of normal collagen. Further, the injury collagen is not remodeled effectively by available collagenase. In addition, inappropriate expression of certain metalloproteinases is a component in the destruction of the joint.

Gene transfer using promoters specific to chondrocytes (i.e., collagen promoters) is used to express different collagens or appropriate collagenase for the purpose of improving the restoration of function in the joints and prevent scar formation.

Gene transfer for these purposes is affected by direct introduction of DNA into the joint space where it comes into contact with chondrocytes and synovial cells. further, the genes permeate into the environment of the joint where they are taken up by fibroblasts, myoblasts, and other constituents of periarticular tissue. Additionally, the gene gun can be used interoperatively or via arthroscopy.

Treatment of Gouty Arthritis by Gene Transfer

Gout is caused by the accumulation of uric acid in joints. This remains a common and painful disorder in the aging population despite medical management. Gene transfer into the joints is used to express products (for example enzymes) capable of degrading uric acid to nontoxic products. These products include urease or urate oxidase which are capable of metabolizing uric acid or urate binding globulins which render this compound more soluble and thus prevent crystalline formation within the joint.

Persistent Expression Using Episomal Vectors

In each of the foregoing examples, transient expression of recombinant genes induces the desired biological response. In some diseases more persistent expression of recombinant genes is desirable. This is achieved by adding elements which enable extrachromosomal (episomal) replication of DNA to the structure of the vector. Vectors capable of episomal replication are maintained as extrachromosomal material and can replicate. These sequences will not be eliminated by simple degradation but will continue to be copied. Episomal vectors provide prolonged or persistent expression, though not necessarily stable or permanent, expression of recombinant genes in the joint. Persistent as opposed to stable expression is desirable to enable adjustments in the pharmacological dose of the recombinant gene product as the disease evolves over time.

Formulations for Gene Delivery into Cells of the Joint

Initial experiments used DNA in formulation for gene transfer into cells of the joint. This DNA is taken up by synovial cells during the process of these cells continually resorbing and remodeling the synovial fluid by secretion and pinocytosis. Gene delivery is enhanced by packaging DNA into particles using cationic lipids, hydrophilic (cationic) polymers, or DNA vectors condensed with polycations which enhance the entry of DNA vectors into contacted cells. Formulations may further enhance entry of DNA vectors into the body of the cell by incorporating elements capable of enhancing endosomal release such as certain surface proteins from adenovirus, influenza virus hemagglutinin, synthetic GALA peptide, or bacterial toxins. Formulations may further enhance entry of DNA vectors into the cell by incorporating elements capable of binding to receptors on the surface of cells in the joint enhances uptake and expression. Alternatively, particulate DNA complexed with polycations can be efficient substrates for phagocytosis by monocytes or other inflammatory cells. Furthermore, particles containing DNA vectors which are capable of extravescating into the inflamed joint can be used for gene transfer into the cells of the joint.

Ablation of Inflammatory Cells Invading the Joint.

Inflammatory cells invading the joint are ablated using vectors which contain the diphtheria toxin gene, other cytopathic genes, or genes capable of inducing apoptosis under the control of a promotor which is expressed only in leukocytes. These vectors are delivered to the joint as particles and are selectively taken up by phagocytotic cells. Uptake can be directed to phagocytic cells by attaching the vector to a protein with trophic properties. The uptake and expression of this vector results in expression of the gene which is lethal to that specific cell. Alternatively, a vector which expressed herpes thymidine kinase gene under the control of a specific promoter could be introduced into cells, and these cells are then ablated by administration of acyclovir.

Inhibiting Inappropriate Proliferation of Synovial cells.

Abnormal proliferation of cells of synovial origin is a common feature of arthritis. This proliferation is treated by introducing a formulated DNA vector into the joint which expresses a growth inhibiting gene product, for example SDI, p53, or Rb. Specific expression is achieved using DNA expression vectors that contain promoters which are activated only in proliferating cells or promoters which are activated only in the presence of an acute phase response, or promoters which are activated only in synovial cells. The expression of these products suppresses proliferation and de-differentiation of cells.

CAT Expression in Various Somatic Targets After Injection of pCMV-CAT.

The expression of CAT and β-gal reporter genes was studied after injection of expression vectors into various organs of the rabbit. CAT activity was assayed in various tissues three days after injection of the pCMV-CAT plasmid. Duplicate experiments were performed for each data point. 200 µg of plasmid at a concentration of 2 µg/ul in a formulation of 20% sucrose was injected into skeletal muscle and produced CAT expression as described by others. (Wolff, I. A., et al., Science, 247:1465–8 (1990)); Jiao, S. et al., Hum. Gene. Ther. 3:21–33 (1992)). No significant CAT activity was detected after injection of the liver, kidney, or salivary gland. CAT activity was observed in the thyroid gland three days after injection at levels equivalent to those in muscle samples in which the same DNA preparation was injected under identical conditions into muscle. This result was consistent whether the level of CAT activity was normalized to the total amount of DNA in harvested tissue (thyroid=69 mU CAT/µg DNA; muscle=80 mU CAT/µg DNA) or total protein in harvested tissue (thyroid=83 mU CAT/mg protein; muscle=80 mU CAT/mg protein). There was no significant difference in the level of activity observed in thyroid after injection of 200 µg of DNA in a formulation containing either PBS or 20% sucrose. The thyroid, unlike most other organs studied, was able to take up purified DNA and express significant levels of CAT activity.

Surgical Procedures and Harvest of Thyroid Tissue

Rabbits (New Zealand white, 5–6 lbs.) were anesthetized with IM Ketamine 25 mg/kg, Xylazine 0.5 mg/kg, Acepromazine 0.6 mg/kg. Using sterile procedures, a lateral neck dissection was performed to visualize the thyroid gland and dissect it free of surrounding fascia, connective tissue, or muscle maintaining its intact capsule and blood supply. A preparation of plasmid DNA (50–200 µg) in 20% sucrose or PBS at a concentration of 2 µg/µl was injected directly into the thyroid gland using a Hamilton 100 µl syringe and 30 gauge disposable needle with 3–4 passes from the inferior to superior pole of the thyroid gland. After ensuring hemostasis, the wound was closed in layers using conventional surgical procedures.

Animals were sacrificed with Nembutal and tissues were harvested for analysis. Tissue for either in situ histochemical analysis or DNA or protein extraction was frozen immediately in liquid nitrogen. Tissue samples for in situ histochemistry were sectioned on a cryostat at 12 µm, fixed, and stained for β-galactosidase expression as described below. Tissue for total DNA or protein extractions was pulverized and then divided for examining CAT expression or DNA elimination.

Protein extracts were prepared from pulverized tissue by rapid freeze/thaw in 0.25M Tris-Cl pH 7.5 buffer, or by sonication in PBS. For sonication, each tissue sample (approx. 100 mg) was minced and suspended in 500 µL sterile PBS in a 1.5 mL microcentrifuge tube on ice, exposed to 4 consecutive pulses of 5 seconds duration each from a Heat Systems-Ultrasonics W-385 sonicator set at 50% power output. Following cell lysis, protein extracts were centrifuged at 9,000 RPM at 4° C. to remove particulate and membrane material. Total protein was quantitated using the Bio-Rad Protein Assay.

DNA was extracted from pulverized tissue by overnight digestion in 10 mM Tris-Cl pH 8.0, 25 mM EDTA, 100 mM NaCl, 0.5% SDS, containing 0.1 mg/ml Proteinase K at 55° C. Protein was denatured and removed by multiple extractions with phenol/chloroform/isoamyl alcohol, precipitated in ethanol, and quantitated based on absorbance pattern at 260 nm wavelength.

Plasmids

An expression vector (pCMV-CAT) containing the CAT gene under transcriptional control of the cytomegalovirus immediate early promotor, the SV40 intron, and the large T polyadenylation sequences has been described previously. (MacGregor, G. R., Somat. Cell. Mol. Genet., 13:253–65 (1987)) An expression vector (pCMVnLacF) containing an E. coli β-gal gene modified to incorporate an SV40 nuclear targeting sequence was constructed by inserting the cytomegalovirus immediate early promotor sequence into the Xba-I site of the clone pnLacF. (Bonnerot C., P.N.A.S., 84:6795–9 (1987))

Plasmid was prepared by alkaline lysis of host bacterial cells and purified by separation on a cesium chloride gradient following overnight centrifugation at 55,000 RPM. DNA was precipitated in 100% ethanol and 300 mM sodium acetate pH 5.3, and stored in $H_2O$ before injection.

CAT and β-Galactosidase Assays

CAT activity was assayed by the conversion of [$^{14}$C] chloramphenicol to mono- and di-acetylchloramphenicol using 50 or 72 µg of protein extract and standard reaction conditions of 1 hour at 37° C. Reaction products were separated on silica-gel TLC in 190:10 chloroform:methanol and quantified using a Betascope 603 Blot Analyzer.

β-gal was assayed in 12 µm frozen sections placed on glass slides. For X-gal staining, tissues were fixed in 2% paraformaldehyde/0.2% glutaraldehyde in 0.1M NaPO$_4$ buffer pH 7.4 containing 0.01% sodium deoxycholate and 0.02% NP-40 for 1 min at room temperature, washed in PBS containing 2 mM MgCl$_2$, stained overnight for β-gal activity in 0.1M NaPO$_4$ buffer pH 7.4 containing 1 mg/ml Xgal, 3 mM K$_3$Fe(CN)$_6$ and K$_4$Fe(CN)$_6$, 1.3 mM MgCl$_2$, 0.01 sodium deoxycholate and 0.02% NP-40, and counterstained with eosin.

DNA Analysis

The concentration of DNA in injected tissues was determined by semi-quantitative PCR by comparing the amount of amplification product in experimental samples with amplifications of control samples containing known amounts of template CAT DNA diluted in normal rabbit genomic DNA. A linear relationship between the concentration of template and amount of amplification in the experimental samples was obtained by optimizing the number of PCR cycles performed (21 cycles for these experiments). The PCR reaction was performed using 1 μg total DNA in 50 μL; 1.1 U Taq DNA polymerase; 200 μM of each dNTP; 1 μg of two primers corresponding to the CAT sequence; denaturation at 94° C. for 6 min; 21 cycles at 94° C. for 1 min, 52° C. for 1 min, and 72° C. for 1 min; and extension at 72 C. for 7 min. Reaction products were analyzed by bidirectional Southern blotting and hybridization using a CAT gene probe in Amersham's Rapid-hyb buffer at 68° C. for 1 hour.

Histological Identification of Cells Expressing Marker Gene After DNA Injection.

Conventional histological examination of injected thyroid tissue demonstrated scattered distortion of normal architecture along the track of injection, with some collapsed follicles as well as small amounts of hemorrhage and histiocytic infiltration. This histology occurs when saline was injected into the gland as a control. To identify which cells were involved in the uptake and expression of the injected DNA vectors, a plasmid expressing nuclear-localizing β-gal was injected into the thyroid, and cells expressing this gene were identified by X-gal histochemical staining of frozen sections. β-gal expression was restricted to the nuclei of cells within a single-cell layer bordering the follicular lumen and was not found in control thyroids injected with plasmid DNA coding for the CAT gene. These cells exhibited the flattened, cuboidal epithelial characteristics of thyroid follicular cells. There was no apparent β-gal expression in endothelial or parafollicular cells of the interstitium separating stained follicles. β-gal expression within a positively-staining follicle involved the majority of cells in the wall of that follicle rather than isolated cells. While there was a very large number of positively staining follicles throughout the thyroid gland, these were not homogeneously distributed but rather were found in discrete regions of the gland, perhaps representing the track of injection. There was considerable variability in the intensity of staining of positive cells which may relate to differences in the level of expression or vagaries in the frozen sections or staining method.

Kinetics of DNA Elimination from Thyroid Tissue and Expression of the Recombinant Gene Product The concentration of DNA and CAT activity in extracts of the thyroid gland was assessed as a function of time after injection. High levels of CAT activity were apparent in most thyroid glands injected with pCMV-CAT in animals sacrificed up to three days after injection. There was no detectable CAT activity over control animals more than ten days after injection. All experimental samples for each time point, regardless of distribution, were combined and averaged for kinetic analysis. There was a clear log-linear relationship between time and the log of CAT activity ($R^2$=0.93), indicative of a first order elimination process having a calculated $t_{1/2}$=46–48 hours.

The concentration of plasmid in whole injected tissues was assessed by semi-quantitative PCR and Southern blotting. Quantitation was obtained using an adaptation of the method of Morgan et al., Hum. Gen. Ther., 1:135–149 (1990) in which the amount of product obtained by limited amplification of experimental samples was compared with the amount of amplification for a simultaneously run standard control curve containing known amounts of plasmid mixed with uninjected rabbit DNA. Significantly, this method identifies DNA molecules in which the 312 base fragment amplified by PCR is intact, and will not measure fragments or nucleotides arising from the injected plasmid. The amount of CAT DNA in the thyroid decreased rapidly during the first 24 hours after injection. The elimination of DNA exhibited first order kinetics as evidenced by the log-linear relationship between time and the log of the concentration of vector sequences ($R^2$ =0.95) with the half life $t_{1/2}$=10 hours (FIG. 3D). By three days after injection, the amount of DNA persisting in the thyroid was <$10^{-8}$ μg plasmid/μg total DNA or $10^2$ copies of plasmid/cell. DNA was extracted from whole thyroid tissue.

Human Growth Hormone Expression in Rat Thyroid

The expression of Human Growth Hormone (hGH) was studied after injection of expression vectors containing the hGH gene into rat thyroids. The expression of hGH was measured 24 hours after injection of CMV-GH plasmid vectors. CMV-CAT vectors were used as a control. Vectors were prepared as described above. Vectors (200 μg) at a concentration of 2 μg/μl in a formulation of 20% sucrose or PBS were injected into the thyroid. Rats were sacrificed 24 hours after injection. Expression of hGH in thyroid tissue was assayed using a commercial hGH antibody kit (Allegro, Nichols Institute).

Figure 12:
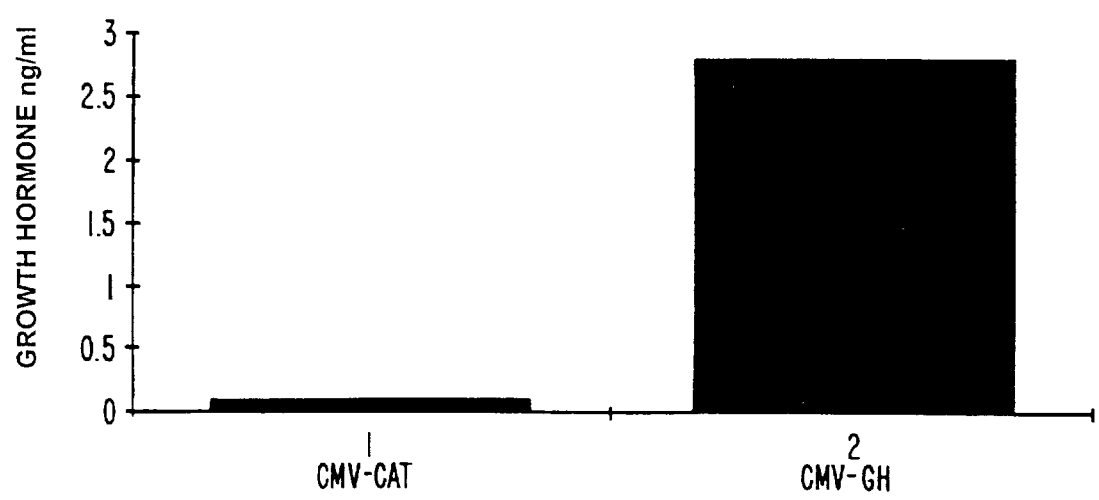
FIG. 12 is a representation of the expression of Human Growth Hormone in rat thyroids transformed with either CMV-CAT vector or CMV-GH vectors.
Figure 13A:
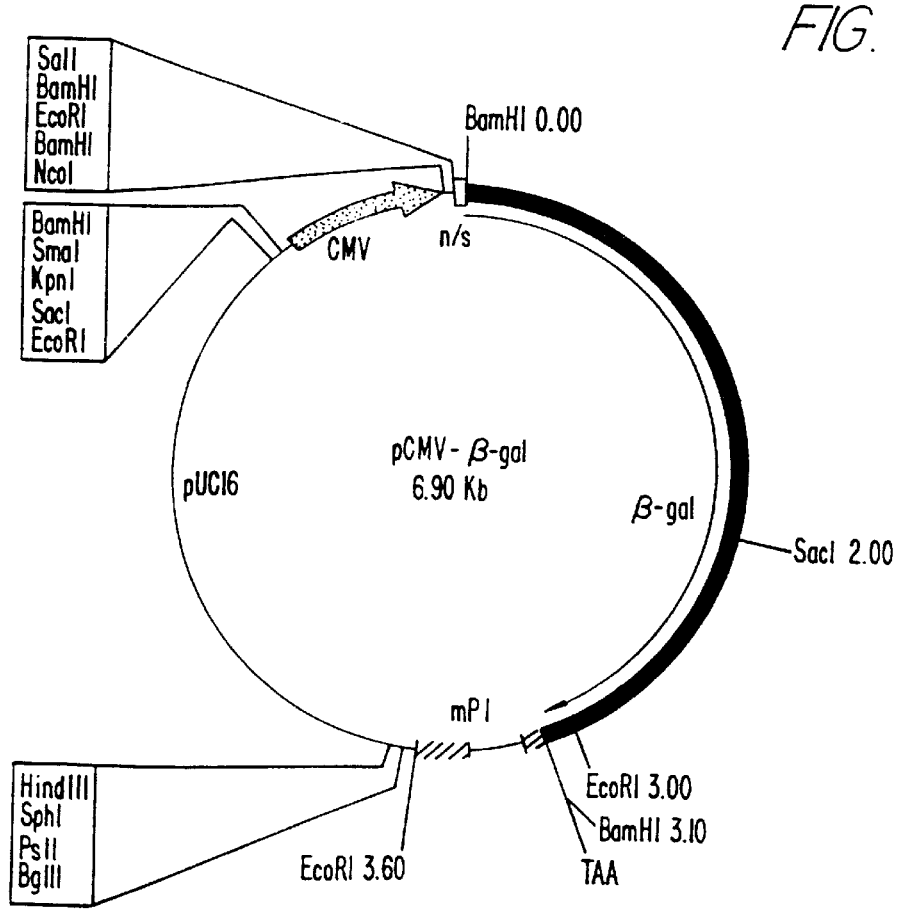
FIG. 13 is a schematic representation of the vector constructs of the present invention.
Figure 13B:
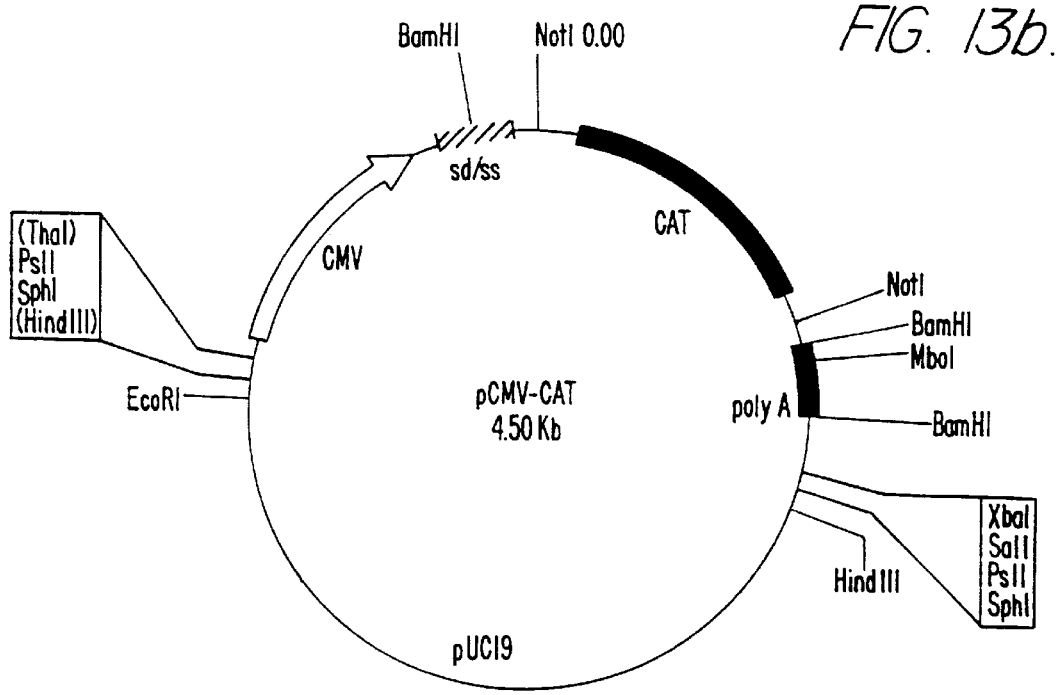

As shown in FIG. 12, hGH was expressed in the rat thyroids directly injected with the above hGH vectors. The control, CMV-CAT, showed no detectable expression of hGH in the thyroid.

Harvest and Cultivation Thyroid Follicular Cells

Thyroids were harvested from mongrel dogs 15–20 kg posteuthanasia and washed in Hanks Balanced Salt Solution (HBSS) containing Penicillin/Streptomycin/Fungizone at 4° C. The tissue was manually dissociated, minced to form a thick slurry, and incubated in a shaking water bath in a solution of HBBS with 1 mg/ml collagenase (CLS 287 U/mg), 1 mg/ml DNAse-1, and 5 mM CaCl$_2$ at 37° C. for 1 hour. Cells were pelleted by centrifugation at 800 rpm for 8 minutes at room temperature. The cell pellet was resuspended in HBBS and dispersed by 3–4 passages through an 18 gauge needle and recentrifuged at 500 rpm for 10 minutes at room temperature. This pellet was resuspended in Coon's modified F-12 supplemented with 0.5% fetal calf serum, 10 μg/ml insulin, 5 μg/ml transferrin, 10 nM hydrocortisone, 1 mU/ml bovine TSH, and antibiotics and plated on Primaria tissue culture plates. Cells were subcultured after trypsinization with trypsin/EDTA, dissociated by 3 passages through an 18 gauge needle. Trypsinization was stopped with media containing 10% serum, and cells were plated in Coon's media with additives including 0.5% fetal calf serum. These thyroid follicular cells were used as is or the serum containing media was replaced after 24 hours with media containing 6 nM selenium in addition to hormones but without serum.

Several technologies for this procedure are available. Generally, one skilled in the art recognizes that surgical resection of a unilateral lobe or segment of the thyroid is a routine procedure associated with minimal morbidity and that follicular cells are isolated and cultivated after surgery. These harvested and cultivated cells are transformed with vectors of the present invention and express the recombinant gene product in vitro.

Transformation with DNA Vectors

A vector, 100–200 µg, containing the E. coli chloramphenicol acetyltransferase gene under the direction of a cytomegalovirus immediate early promotor was diluted in 100 µl of formulation containing 20% sucrose. A schematic of this vector is shown in FIG. 8.

The thyroid of rabbits was approached surgically with a lateral incision and visualized. 100 µl of the vector containing formulation was injected directly into the gland under direct observation through insertions in both the superior and inferior poles of the gland. After ensuring that hemostasis was preserved the incision was closed and the animal allowed to recover from anaesthesia. Identical procedures were performed in the contralateral gland. Control experiments were performed with sterile saline or vectors containing unrelated genes.

1–30 days after the gene transfer the animals were sacrificed and the thyroid were harvested for analysis. The glands were frozen in liquid nitrogen, pulverized, and material allocated for DNA and protein analysis. The activity of chloramphenicol acetyl transferase was measured as was the amount of total protein. Chloramphenicol acetyltransferase DNA was identified by southern blotting and PCR.

Expression of CAT enzyme activity was observed in animals injected with the expression vector but not in control animals. Activity was present at 1 and 3 days but decreased thereafter and no activity was apparent after 14 days. The level of DNA estimated by southern blotting paralleled the level of enzyme activity.

Targeting Somatic Gene Therapy to the Thyroid

DNA protein complexes are prepared containing thyroglobulin, polylysine and DNA or, alternatively, thyrotropin, polylysine and DNA. Covalent binding of polylysine and thyroglobulin or thyrotropin was performed using conventional methods for protein coupling. DNA is then bound to this complex non-covalently by virtue of the positive charge on polylysine.

The complexes are injected into the peripheral veins of an experimental animal. The binding of the thyrotropin or thyroglobulin determinants to specific receptors on the thyroid follicular cells causes receptor mediated uptake of the complex. Following uptake some DNA escapes catabolism in the endosome and the gene product encoded by the DNA is expressed.

Transient Gene Therapy for Congenital Hypothyroidism

Two experimental mouse models exist for congenital hypothyroidism. The hyt mouse is presumed to be deficient in the thyrotropin receptor and has atretic thyroid glands. The cog mouse has been shown to be deficient in the thyroglobulin gene and has goiter. Gene therapy of congenital hypothyroidism in the hyt mouse is performed using vectors containing a cassette encoding the thyrotropin receptor. Similarly, gene therapy of congenital hypothyroidism in the cog mouse is performed using plasmids containing a nucleic acid cassette encoding a normal thyroglobulin protein. In either case the vector is injected into the body of the thyroid gland. During a period of transient expression these genes are expressed, thereby replacing the genetically defective function, and enabling these cells to produce thyroid hormone. One skilled in the art will recognize that the various causes of inherited congenital hypothyroidism is treated by replacement of the essential gene product by transient somatic gene therapy.

Transient Gene Therapy for Hemophilia by Thyroid Gene Transfer

A vector containing the open reading frame from clotting factor VIII and an appropriate promotor capable of directing gene expression in thyroid cells is injected into the body of the thyroid. Injection of this gene into the thyroid of patients with hemophilia (factor VIII deficiency) will cause the thyroid to secrete factor VIII into the serum where it will replace the genetically defective function. The level of expression is determined by the dose of DNA and choice of promoter elements included in the vector. This expression is transient but can be used to replace essential functions in conjunction with surgery or in response to specific complications such as intracranial bleeding or bleeding into joints. One skilled in the clinical care of patients with hemophilia will recognize the importance of providing clotting factors to treat serious bleeding episodes in these patients.

Transient Expression of Endorphins (Enkephalins) for Analgesia

Vectors containing the open reading frame encoding an endorphin under control of a promotor are injected into the body of the thyroid. Cells taking up this DNA will express endorphins and secrete these proteins into the blood where they target the brain and provide analgesia. Since this effect is transient, analgesia will be provided for several days with this method. The level of analgesia is determined by the dose of DNA administered as well as the use of different promoters within the DNA vector.

Enhancement of Lactation by Transient Expression of Prolactin

DNA vectors with a suitable promotor and a nucleic acid cassette containing the prolactin gene sequence can be introduced into the thyroid by direct injection or by targeted delivery involving intravenous injection of vector coupled to thyrotropic proteins. Uptake of the vector by the thyroid will result in transient expression of prolactin for a period of 3–5 days. Administration of this agent at the time of parturition could facilitate the early phases of nursing, improve infant nutrition, and enhance the ability of many to breast feed. After the period of transient expression, enhanced prolactin expression from the thyroid will cease and normal mechanisms regulating lactation will ensue.

Development of Vectors for Thyroid Gene Therapy from Thyroid Specific Regulatory Elements Vectors for expressing nucleic acid sequences within the thyroid which are constructed using thyroid specific elements enable regulation of expression in response to elements which normally regulate the thyroid, specifically thyrotropin. For example, vectors containing the promotor from the thyroglobulin gene are designed to increase the level of gene expression in response to thyrotropin. In contrast, vectors containing the promotor from the thyrotropin receptor gene are designed to decrease the level of expression in response to thyrotropin. Since thyrotropin secretion is one of the major determinants of the basal metabolic rate, this mechanism could be used to either increase or decrease the expression of recombinant nucleic acid sequences in response to metabolic stress.

Somatic Gene Therapy to the Ear

The auditory system is comprised of a network of sensorineuroepithelium (i.e., hair cells), supporting cells, distinct afferent and efferent sensory neurons, and adjacent vascular and connective tissue elements contained mostly within the cochlea. The generalized pathologic process in hearing loss is that of hair cell loss or destruction within the cochlear system. Congenital infections and genetic diseases, other infections (meningitis, otitis media, labyrinthitis), systemic diseases like diabetes, trauma, ototoxicity from certain drug therapy's (i.e., antibiotics and chemotherapeutic drugs), and the senescence of aging all result in the destruction or deterioration of the hair cells and their surrounding components to variable degrees. Hair cells that have been damaged or lost as a result of the above mentioned processes, can be regenerated or rejuvenated using gene therapy. Vectors as described above which encode for nerve growth factor (NGF) or other trophic factors such as IGF-1, IGF-2, TGF-alpha, or TGF-beta can be directly injected to stimulate sensory nerve growth. Furthermore these factors also affect the growth or recovery of the supporting and surrounding cells and sensory neurons linking the brainstem. The survival or regeneration of the specific hair cells improves the collective action of the inner ear apparatus and thus results in increased hearing.

In one specific embodiment loss of hearing in diabetic populations such as the elderly, and certain trauma incidents or intracerebral vascular events can be caused due to loss of blood supply to the organ of corti (i.e., inner ear hearing apparatus). Direct injection of vectors which increase blood delivery/induced local angio-genesis as well as corresponding hair, nerve, supporting cell growth will reverse or at least arrest the progressive hearing loss. Vectors which express NGF, platelet-derived growth factor (PDGF), epidermal growth factor, IGF-1, IGF-2, insulin, fibroblast growth factors, TGF-alpha, TGF-beta or IL-1, IL-1 receptor antagonist, IL-1 soluble receptor can be used.

The vestibular system is also comprised of its distinct network of sensorineuroepithelium and supporting cells, sensory nerves, and connective tissue and vascular elements. Destruction, alteration, or general deterioration of any of these elements will after the functioning of the vestibular apparatus. Vestibular disorders ranging from simple dizziness or unbalance to actual vertigo can be severely debilitating. By use of vectors as described above directly injected into the vestibular system elements result in regeneration of the affected vestibular cells and reverses or at least improves the vestibular disorders.

Vectors as described above can also be used in reversing or arresting the progression of diseases involving both a cochlear and vestibular systems. One embodiment involves endolymphatic hydrops (Meniere's disease) which results from over production of endolymph within the membranous inner ear system. Vectors can be directly injected into the vestibular system which express a protein or RNA which can reduce the local production of endolymph or increase the resorption of endolymph within the membranous inner ear system. These vectors greatly improve the disease symptoms of dizziness, vertigo and fluctuating hearing loss.

Use of a vector expressing NGF could be used to promote growth and recovery of sensory neurons and neuronal elements (microfilaments-kinocilia) including auditory and vestibular epithelium. Vectors expressing NGF can also be used to stimulate regeneration or growth of ganglion (spiral ganglion) cell bodies involved in the transmission of auditory stimulus. Other factors such as ciliary nerve growth factor and insulin-like growth factor IGF-1 can also be used for the above results.

Vectors expressing platelet-derived growth factor (PDGF) can be utilized to stimulate the proliferation of injured or severed epi-, peri-, and endoneural connective tissue. Vectors expressing growth factors such as EGF, IGF-1, IGF-2, insulin, fibroblast growth factors, TGF-alpha or TGF-beta can be utilized to increase the regeneration, revascularization, and functional recovery of injured nerve tissue or hair cell epithelium. Furthermore vectors expressing antiflammatory factors such as receptor antagonist for IL-1 (PG, IL-1RA, IL-1 soluble receptor). Expression of synthetic steroid receptors increases sensitivity to system steroids or constitutive activity expressed in the absence of pharmacological steroids.

Gene Therapy to the Eye

Gene therapy using the vectors as described above can be used to transfer genes expressing therapeutic products into the structures of the eye for the purposes of treating congenital, acquired, or degenerative causes of blindness or visual deficit. Furthermore gene transfer by this method can be used to enhance the growth, regeneration, repair, or function of the optic nerve and retinal tissues including photoreceptor and nerves that have been damaged or are deteriorating as a result of aging, infection, trauma, surgery, or other systemic disorders. Gene therapy by this method also applies to the lens and connective tissues which are involved in diseases such as glaucoma and cataracts. Furthermore gene therapy by this method applies to inflammatory disorders of the eye, cornea, retinal, conjunctiva, tear ducts, or sclera. Gene transfer can be used to secrete anti-angiogenic factors such as interferon $\alpha$ or $\beta$ or thrombospondin that would control or reverse neovascularization within the eye, a common cause of visual loss. The size and strength of ocular muscles can be enhanced to correct strabismus and prevent amblyopia by using gene therapy to the eye. Furthermore gene transfer into muscles of the cornea can be used to treat defects associated with aging or injury. Genes that can be utilized in the above described vectors include NGF, TDGF, TGF-$\alpha$, TGF-$\beta$, fibroblast growth factors, IGF-1, IGF-2, insulin, transferrin, receptors for angiostatic steroids, peptide backbones for peptidoglycan, platelet factor 4, angiogenesis modulator factors and anti-inflammatory factors such as receptor antagonist for IL-1 (IL-1RA, IL-1 soluble receptor).

Retinal or optic nerve regeneration can be treated using gene therapy to the eye. The retina is a multi-layer structure with a base layer of pigment epithelium beginning anterior to the choroid. This layer is followed by the neurosensory layer of interneurons which connect the photoreceptor cells to ganglion cells which comprise the most anterior layer of the retina. Retinal degeneration or destruction can result from a multitude of diseases or pathological processes including glaucoma, diabetes, general vitriol retinal disease, and genetic disorders (e.g., retinitis pigmentosa). Vectors described above can be applied to stimulate regrowth of regenerating retinal sensory neural tissue by providing local secretion of growth and reparative factors as described above.

Ocular damage post surgery or trauma can also be treated using the above referenced vectors. Commonly after trauma, cataract or other surgery, local inflammatory processes can result in destruction of ocular tissues and loss of visual acuity. Direct DNA delivery using formulated DNA expression vectors expressing factors that suppress or modulate the inflammatory response can be used to reduce the destructive visual sequelae.

Gene therapy to the eye can be used to control or suppress glaucoma. In general, glaucoma occurs because of a decrease in the outflow of aqueous fluid drainage through trabecular meshwork. Certain theories ascertain that macromolecules (e.g., glycosaminoglycans pigments) occlude this meshwork and mechanically obstruct the aqueous flow causing an increase in intraocular pressure. The increased pressure results in retinal and local tissue damage and thus blindness. Gene therapy using the above vectors can be used by local injection or even cellular transplantation into the ciliary body which would result in decreased production of aqueous fluid from the ciliary epithelium to lower intraocular pressures. In addition, gene therapy using the above vectors directed at suppressing the production and/or secretion of these glycosaminoglycans prevents blockage of the normal outflow filtering process.

Neovascularization is one of the most common causes of acquired blindness, and is not limited to diabetics. Age related macular degeneration (AMD) is caused by new vessel formation originating from choroidal vessels as a result of breaks in "Brooks" membrane. Diabetic retinopathy results from neovascularization that is a response to local ischemia and its effects on the secretion of factors from retinal ganglion cells/vascular endothelium. This new vessel proliferation originates from retinal vascular tissue and grows within the retina and into vitreous fluid causing local destruction. Gene therapy with the above vectors directed at delivery of antiangiogenic factors locally to the retina or choroid arrests further damage and even reverses the neovascularization and subsequent blindness.

A specific cause of blindness occurs predominantly in diabetics after surgical procedures such as vitrectomy and tractional retinal detachment repair. In these circumstances the surgical procedure can stimulate a massive fibrin response with local deposits and return of retinal tractions that cause a significant loss of vision if not controlled. Present treatment consists of repeated daily injections of TPA into the anterior chamber to dissolve the fibrin deposits and quell the response. The multiple injection carries associated morbidity and expense of multiple office visits, procedural costs, and actual pharmaceutical costs. Direct injection of the above vectors results in transient secretion of enzymes or plasminogen activators to dissolve the fibrin deposits. This eliminates the need for multiple injections and would provide continual release and thus maintain higher levels, thus improving overall efficiency.

Gene therapy to the eye can also be used to treat strabismus and prevent amblyopia. Strabismus is a disorder in children characterized by weakness of muscles controlling movement of the eye (commonly known as "lazy eye"). The failure of ocular muscles to provide for coordinated eye movement leads to the preference of a single eye for effective vision with subsequent loss of function of the other eye. This is commonly treated with a surgical procedure in which an incision is made around the eye and the muscle is shortened to provide increased pressure on the eye. Introduction of genes for IGF-1 into the relatively weak muscle enables this muscle to develop normal tone and function and prevent the need for surgical procedures in children.

Accommodation of the eye to focusing at different distances involves a series of muscles linked to the lens. The failure of this process especially with aging can be treated using the vectors described above. By direct injection of a vector containing a gene which encodes for IGF-1 into specific muscle groups the function of these muscles can be enhanced.

Gene therapy to the eye for treatment of cataracts can be used. Cataracts result from the deposition of insoluble and opaque material within the lens of the eye. This can be caused by metabolic diseases as in galactosemia in which unmetabolized galactose accumulates within the lens. In diabetes, cataracts may result from the accumulation of particular proteins, such as in common senile cataracts. Current therapy involves the surgical removal of the lens. While this is a relatively minor surgical procedure, it results in imperfect vision without the capacity for accommodation and frequently results in glaucoma. Somatic gene therapy using direct delivery of vectors described above which introduce genes for enzymes capable of digesting the insoluble and opaque material into the cells lining the joint, the aqueous compartment, or associated glands which synthesize the aqueous fluid can be used to treat cataracts. The enzyme synthesized in these sites diffuses into the cataract thus preventing the need for surgical removal.

Cell Transformation

One embodiment of the present invention includes cells transformed with the vectors described above. Once the cells are transformed, the cells will express the protein or RNA encoded for by the nucleic acid cassette.

The nucleic acid cassette which contains the genetic material of interest is positionally and sequentially oriented within the vectors such that the nucleic acid in the cassette can be transcribed into RNA and, when necessary, be translated into proteins in the transformed cells. A variety of proteins can be expressed by the sequence in the nucleic acid cassette in the transformed cells. These products may function as intracellular or extracellular structural elements, ligands, hormones, neurotransmitters, growth regulating factors, enzymes, serum proteins, receptors, carriers for small molecular weight compounds, drugs, immunomodulators, oncogenes, tumor suppressors, toxins, tumor antigens, antigens, antisense inhibitors, triple strand forming inhibitors, ribozymes, or as a ligand recognizing specific structural determinants on cellular structures for the purpose of modifying their activity. One skilled in the art will be familiar with techniques for transformation.

Administration

Administration as used herein refers to the route of introduction of a vector or carrier of DNA into the body. Administration may include intravenous, intramuscular, topical, or oral methods of delivery. Administration can be directly to a target tissue or through systemic delivery.

In particular, the present invention can be used for treating disease or for administering the formulated DNA expression vectors capable of expressing any specific nucleic acid sequence. Administration can also include administering a regulatable vector discussed above. Such administration of a vector can be used to treat disease. The preferred embodiment is by direct injection to the target tissue or systemic administration.

A second critical step is the delivery of the DNA vector to the nucleus of the target cell where it can express a gene product. In the present invention this is accomplished by formulation. The formulation can consist of purified DNA vectors or DNA vectors associated with other formulation elements such as lipids, proteins, carbohydrates, synthetic organic compounds, or in-organic compounds. Examples of such formulation elements include, but are not limited to, lipids capable of forming liposomes, cationic lipids, hydrophilic polymers, polycations (e.g. protamine, polybrine, spermidine, polylysine), peptide or synthetic ligands recognizing receptors on the surface of the target cells, peptide or synthetic ligands capable of inducing endosomal-lysis, peptide or synthetic ligands capable of targeting materials to the nucleus, gels, slow release matrices, soluble or insoluble particles, as well as other formulation elements not listed. This includes formulation elements for enhancing the delivery, uptake, stability, and/or expression of genetic material into cells.

The delivery and formulation of any selected vector construct will depend on the particular use for the expression vectors. In general, a specific formulation for each vector construct used will focus on vector uptake with regard to the particular targeted tissue, followed by demonstration of efficacy. Uptake studies will include uptake assays to evaluate cellular uptake of the vectors and expression of the tissue specific DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

DNA uptake by cells associated with fluid spaces have the unique ability to take up DNA from the extracellular space after simple injection of purified DNA preparations into the fluid spaces. Expression of DNA by this method can be sustained for several months.

Incorporating DNA by formulation into nanoparticle complexes that undergo endocytosis increases the range of cell types that will take up foreign genes form the extracellular space.

Formulation can also involve DNA transporters which are capable of forming a non-covalent complex with DNA and directing the transport of the DNA through the cell membrane. This may involve the sequence of steps including endocytosis and enhanced endosomal release. It is preferable that the transporter also transport the DNA through the nuclear membrane. See, e.g., the following applications all of which (including drawings) are hereby incorporated by reference herein: (1) Woo et al., U.S. Ser. No. 07/855,389, entitled "A DNA Transporter System and Method of Use" filed Mar. 20, 1992; (2) Woo et al., PCT/US93/02725, entitled "A DNA Transporter System and method of Use", (designating the U.S. and other countries) filed Mar. 19, 1993; and (3) continuation-in-part application by Woo et al., entitled "Nucleic Acid Transporter Systems and Methods of Use", filed Dec. 14, 1993, assigned attorney docket number 205/012 but not yet assigned a U.S. Ser. No.

In a preferred method of administration involving a DNA transporter system, the DNA transporter system has a DNA binding complex with a binding molecule capable of non-covalently binding to DNA which is covalently linked to a surface ligand. The surface ligand is capable of binding to a cell surface receptor and stimulating entry into the cell by endocytosis, pinocytosis, or potocytosis. In addition, a second DNA binding complex is capable of non-covalently binding to DNA and is covalently linked to a nuclear ligand. The nuclear ligand is capable of recognizing and transporting a transporter system through a nuclear membrane. Additionally, a third DNA binding complex may be used which is also capable of non-covalently binding to DNA. The third binding molecule is covalently linked to an element that induces endosomal lysis or enhanced release of the complex from the endosome after endocytosis. The binding molecules can be spermine, spermine derivatives, histones, cationic peptides and/or polylysine. See also Szoka, C. F., Jr. et al., Bioconjug. Chem. 4:85–93 (1993); Szoka, F. C., Jr. et al., P.N.A.S., 90:893–897 (1993).

Transfer of genes directly has been very effective. Experiments show that administration by direct injection of DNA into joints and thyroid tissue results in expression of the gene in the area of injection. Injection of plasmids containing IL-1 into the spaces of the joints results in expression of the gene for prolonged periods of time. The injected DNA appears to persist in an unintegrated extrachromosomal state. This means of transfer is the preferred embodiment.

The formulation used for delivery may also be by liposomes or cationic lipids. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active. Cationic lipid formulations such as formulations incorporating DOTMA has been shown to deliver DNA expression vectors to cells yielding production of the corresponding protein. Lipid formulations may be non-toxic and biodegradable in composition. They display long circulation half-lives and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system. See Szoka, F. C., Jr. et al., Pharm. Res., 7:824–834 (1990); Szoka, F. C., Jr. et al., Pharm. Res., 9:1235–1242 (1992).

The chosen method of delivery should result in cytoplasmic accumulation and optimal dosing. The dosage will depend upon the disease and the route of administration but should be between 1–1000 mg/kg of body weight/ day. This level is readily determinable by standard methods. It could be more or less depending on the optimal dosing. The duration of treatment will extend through the course of the disease symptoms, possibly continuously. The number of doses will depend upon disease, the formulation and efficacy data from clinical trials.

With respect to vectors, the pharmacological does of a vector and the level of gene expression in the appropriate cell type includes but is not limited to sufficient protein or RNA to either: (1) increase the level of protein production; (2) decrease or stop the production of a protein; (3) inhibit the action of a protein; (4) inhibit proliferation or accumulation of specific cell types; and (5) induce proliferation or accumulation of specific cell types. As an example, if a protein is being produced which causes the accumulation of inflammatory cells within the joint, the expression of this protein can be inhibited, or the action of this protein can be interfered with.

Viral Vectors

The following are other examples of gene delivery using viral vectors. These are disclosed herein as examples only and are a different invention.

If retroviral vectors are used, the nucleic acid can be stably incorporated into, for example, thyroid folliculocytes, by recombinant virus having a recombinant genome positionally and sequentially oriented for expression of a nucleic acid cassette. The retrovirus includes two long terminal repeat sequences, a sequence capable of packaging a retroviral particle, (e.g., Y packaging sequence), at least one promoter, and a nucleic acid cassette encoding a protein, polypeptide or RNA. The retroviral embodiment may include a selectable marker for chemical, pharmacological, or fluorescent elimination of non-transduced cells and/or other retroviral sequences required for integrity and function of the retroviral vector.

Transformation with Retroviral Vectors

The LNL6/PA317/6c cell line producing the LNL6 defective retroviral vector which carries the *E. coli* neomycin phosphoribosyltransferase gene (NEO-R) was used. (Miller and Rossman *Biotechniques* 7, 980–990, 1989). This vector was titered on NIH3T3 cells and G418 selection using standard procedures (Miller and Rossman *Biotechniques* 7, 880–990, 1989). A cell line producing an amphotropic zen-βgal defective retroviral vector which carries the *E. coli*β-galactosidase gene (β-gal) was titered by transduction of NIH3T3 cells and counting β-gal colonies with histochemical stain. These vectors are shown schematically in FIG. 7. The vector was harvested from media conditioned on these cell lines for 12–18 hours. Transduction was performed by adding this vector containing media to cells diluted 1:1 with cell culture media with the addition of polybrene at 8 $\mu$g/ml. Transductions were performed for 12–18 hours at which time cells were fed with fresh media.

Thyroglobulin staining was performed using a mouse anti-human thyroglobulin monoclonal antibody (SIGMA) (1:500) or rabbit anti-human thyroglobulin (1:500) and anti-IgG coupled to alkaline phosphatase (1:1000). Staining was performed using NBT and BCIP.

Staining for cells expressing B-gal was performed with X-gal as described (MacGregor et al. Somat. Cell Mol. Genet. 13:253–265(1987)). The presence of the LNL6 provirus in transduced cells was detected by semi-quantitative PCR using the method described by Morgan et al. Hum. Gen., Ther. 1, 135–149 (1990).

Transduction with Amphotropic Retrovirus

Thyrocyte cultures were transduced with recombinant retrovirus using methods previously described above for other primary cells.

To obtain higher efficiency transduction thyrocyte cultures were transduced with the LNL6 retroviral vector carrying the NEO-R gene at a titer of $10^7$ pfu/ml. The fraction of cells successfully transduced with this vector was estimated by identification of the recombinant provirus integrated in cellular DNA by PCR. Semi-quantitative analysis was achieved by amplification of control DNA known to contain one provirus/genome, and sequential dilutions of this DNA with non-transduced DNA. Negative controls included non-transduced thyrocyte cultures, and blank reactions run with all reagents in the absence of DNA. Proviral sequences were apparent in transduced cells grown in the presence or absence of serum 6 and 12 days after transduction. There was no notable decrease in proviral fraction during cultivation. The intensity of PCR amplification was roughly equivalent to that observed with a 1:10 dilution of the control sample containing 1 provirus/cell suggesting that approximately 10% of cells were transduced.

Selection of Transduced Thyrocytes With G418

The cells transduced with LNL6 as discussed above were selected with G418. Optimal conditions for G418 selection were determined. Generally, rapid cell death (2–3 days) was observed with concentrations of G418 >800 $\mu$g/ml, and incomplete selection was achieved with concentrations $\leq$200 $\mu$g/ml after 10 days of selection. Cultures transduced with LNL6 and subjected to selection with 400–600 $\mu$g/ml G418 for 10–12 days exhibited viable cells while there was complete killing of non-transduced cells.

Cultures of selected cells exhibited morphology similar to that of non selected cells by phase contrast microscopy. Immunostaining with anti-TG demonstrated persistent expression of TG in >50% of cells. PCR analysis demonstrated that frequency of the provirus in selected cells approached 1 copy/cell.

A further demonstration of expression of the recombinant gene in transduced cells was seen in NEO-R expression on unselected/selected cells using the NEO-R assay or northern blot.

Transplantation and Engraftment of Transduced Thyroid Folliculocytes

Thyroid follicles were harvested after unilateral lobectomy in dogs and placed in culture in media containing 0.5% serum and thyrotropin. After 5–10 days cells were trypsinized, dispersed into monolayers, and replaced in culture media. Transduction was performed by exposing cells to media conditioned on a cell line (LNL6/PA317/6c) producing the LNL6 retroviral vector with the neomycin resistance gene in the presence of 8 $\mu$g/ml polybrene. 2–5 days after transduction cells were again recovered by trypsinization and transplanted into the contralateral lobe of autologous animals by direct injection into the body of the thyroid. Animals were sacrificed 7–14 days after transplantation and the thyroid was harvested. The thyroid gland was frozen in liquid nitrogen, pulverized, DNA was isolated by conventional methods, and the presence of the LNL6 provirus integrated in thyroid tissue was assayed by PCR. The presence of the gene in these tissues demonstrates that the transduced and transplanted cells had successfully engrafted within the thyroid gland.

In Vivo Transduction of Thyroid Folliculocytes

The thyroid gland or the rabbit was surgically visualized after a lateral incision and blunt and sharp dissection. 100 $\mu$l of a preparation containing an amphotropic retrovirus containing the neomycin resistance gene was injected through insertions in the superior and inferior poles of the gland. At intervals after injection the animals are harvested and the presence of the virus was assayed using the polymerase chain reaction.

Retroviral integration is critically dependent upon division of the target cell. To induce proliferation of the thyroid, animals are treated with a pharmacological agent (methimazole) or a thyrotrophic hormone (thyrotropin) at an optimal interval prior to retroviral injection.

Stable Gene Therapy for Congenital Hypothyroidism

Retroviral vectors are constructed containing the open reading frame for the thyrotropin receptor. The vector constructs are introduced into a appropriate packing cell line to produce ecotropic or amphotropic defective retroviral particles.

For gene therapy the thyroids of hyt animals are harvested and cultivated in vitro. Cells are exposed to conditioned media from the vector producing cell line in the presence of polybrene 8 μg/ml. After expansion of primary cultures, cells are trypsinized ad transplanted into an orthotopic or heterotopic location of congenic hyt mice. The replacement of the thyrotropin receptor gene allows these cells to proliferate in response to endogenous thyrotropin and to produce thyroid hormone normally. One skilled in the art will recognize that various forms of inherited congenital hypothyroidism are treatable by replacement of the essential gene product by stable gene therapy.

Stable Gene Therapy for Factor IX Deficiency by Ex Vivo Transduction

Thyroid cells are harvested by biopsy of the thyroid gland from a patient with factor IX deficiency. These cells are expanded in primary culture and transduced with a retroviral vector containing the open reading frame of the factor IX gene. If the retroviral vector contains in addition the gene for neomycin resistance gene, transduced cells can be selected with G418. After further expansion of the primary cultures cells are harvested by trypsinization and transplanted orthotopically into the thyroid gland or heterotopically into another location. Cells transduced with the vector containing the factor IX gene will secrete this protein into the serum where it will replace the genetically defective function. The gene is stably integrated into the transplanted cells and continuously secretes the essential clotting factor into the blood.

Stable Gene Therapy for Factor IX Deficiency by In Vivo Transduction

Patients are pretreated with a pharmacological or hormonal regiment to stimulate proliferation of thyroid follicular cells, This involves administration of methimazole, thyrotropin or thyrotropin releasing hormone. At an appropriate time after administration of these agents a retroviral vector containing the open reading frame of the factor IX gene is injected into the body of the thyroid gland. The injected retroviral vector will stably integrate into a fraction of cells and these cells continuously secrete factor IX into the serum where it can replace the genetically defective function. Removal of the thyrotropic agents will return thyroid function to normal.

Stable Gene Therapy for Type I Diabetes

Retroviral vectors are constructed containing the insulin gene as well as promoters capable of regulating the expression of insulin in response to appropriate metabolic, endocrine, and paracrine factors. This construct is introduced into a packaging cells line to produce amphotropic defective retroviral vectors. These vectors can be delivered to the thyroid gland in vivo by direct injection or ex vivo by transduction and transplantation of thyroid follicular cells. Cells taking up this gene will express insulin. Since the thyroid shares many developmental and endocrine features of the pancreas, regulated expression of insulin may be achieved. Since this gene transfer is stable, this will be a stable cure for insulin deficiency.

All patents and publications mentioned in this specification are indicative of the levels of those skilled in the art to which the invention pertains. All patents and publications are herein incorporated by reference to the same extent as if each individual publication was specif ically and individually indicated to be incorporated by reference.

One skilled in the art will readily appreciate that the present invention is well adapted to carry out the objects and obtain the ends and advantages mentioned, as well as those inherent therein. The transformed thyroid folliculocytes; transformed synoviocytes; transformed cells associated with the ear, eye formulated DNA express vectors; along with the methods, procedures, treatments, molecules and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method for gene delivery and transient gene expression comprising the steps of introducing a DNA expression vector into a fluid space formed by the vitreous of the eye under conditions in which cells associated with said fluid space transiently incorporate said DNA expression vector into said cells and transiently expressing, from said expression vector, said gene inside said cells; wherein said DNA expression vector comprises:

a nucleic acid cassette;

a 5' flanking region including necessary sequences for expression of said nucleic acid cassette;

a linker connecting said 5' flanking region to said nucleic acid cassette, said linker having a position for inserting said nucleic acid cassette, wherein said linker lacks the coding sequences of a gene with which it is naturally associated; and a 3' flanking region which is 3' to said position for inserting said nucleic acid cassette.

2. The method of claim 1, further comprising introducing said DNA expression vector with a formulation element for facilitating transient incorporation of said DNA expression vector into said cell.

3. The method of claim 1 or 2, wherein said fluid space is an extracellular space enclosed by a cellular membrane.

4. The method of claim 1 or 2, wherein said cells transiently incorporate said DNA expression vector by absorption.

5. The method of claim 1 or 2, wherein said cells transiently incorporate said DNA expression vector by endocytosis or pinocytosis.

6. The method of claim 1 or 2, wherein said DNA expression vector is transiently incorporated into said cells by filtering said DNA expression vector through a membrane comprised of said cells.

7. The method of claim 1 or 2, wherein said DNA expression vector is introduced by direct injection.

8. The method of claim 1 or 2, further comprising regulating gene expression of said nucleic acid cassette by expressing a nucleic acid sequence encoding a modified receptor.

9. The method of claim 8, wherein said modified receptor includes a modified ligand binding domain.

10. The method of claim 8, wherein said modified receptor is a glucocortico-mimetic receptor.

11. A method of transiently transforming a cell associated with a fluid space comprising the steps of introducing a DNA expression vector into said fluid space formed by the vitreous of the eye, contacting said cell with said DNA expression vector for a sufficient time to transiently transfect said cell, and transiently expressing said gene from said expression vector inside said transfected cell; wherein said DNA expression vector comprises:

a 5' flanking region including necessary sequences for expression of a nucleic acid cassette;

a linker connecting said 5' flanking region to said nucleic acid cassette, said linker having a position for inserting said nucleic acid cassette, wherein said linker lacks the coding sequences of a gene with which it is naturally associated; and a 3' flanking region which is 3' to said position for inserting said nucleic acid cassette.

12. A method of transiently transforming a cell associated with a fluid space comprising the steps of introducing a DNA expression vector into said fluid space formed by the vitreous of the eye, wherein said vector is introduced with a formulation element for facilitating transient transfection, contacting said cell with said DNA expression vector for a sufficient time to transiently transfect said cell, and transiently expressing, from said expression vector, said gene inside said transfected cell; wherein said DNA expression vector comprises:

a 5' flanking region including necessary sequences for expression of a nucleic acid cassette;

a linker connecting said 5' flanking region to said nucleic acid cassette, said linker having a position for inserting said nucleic acid cassette, wherein said linker lacks the coding sequences of a gene with which it is naturally associated; and a 3' flanking region which is 3' to said position for inserting said nucleic acid cassette.

13. A cell, wherein said cell is associated with a fluid space formed by the vitreous of the eye, and is transiently transformed with a DNA expression vector for expression of a nucleic acid sequence, wherein said nucleic acid sequence is transiently expressed within said cell, wherein said cell may optionally be removed from said fluid space; and wherein said cell comprises:

a nucleic acid cassette;

a 5' flanking region including necessary sequences for expression of a nucleic acid cassette;

a linker connecting said 5' flanking region to said nucleic acid cassette, said linker having a position for inserting said nucleic acid cassette, wherein said linker lacks the coding sequences of a gene with which it is naturally associated; and a 3' flanking region which is 3' to said position for inserting said nucleic acid cassette.

14. A transiently transformed cell of claim 13 wherein said cell is removed from said fluid space.

* * * * *